US009613188B2

(12) United States Patent
Bradshaw et al.

(10) Patent No.: US 9,613,188 B2
(45) Date of Patent: *Apr. 4, 2017

(54) NEUROIMAGING DATABASE SYSTEMS AND METHODS

(71) Applicant: CereScan Corporation, Denver, CO (US)

(72) Inventors: Vincent Bradshaw, Lakewood, CO (US); Theodore Henderson, Centennial, CO (US); Jennifer Faherty, Greenwood Village, CO (US); Donald Bitto, Pueblo West, CO (US); Nikki Villegas-Mauter, Northglenn, CO (US)

(73) Assignee: CERESCAN CORPORATION, Denver, CO (US)

( * ) Notice: Subject to any disclaimer, the term of this patent is extended or adjusted under 35 U.S.C. 154(b) by 174 days.

This patent is subject to a terminal disclaimer.

(21) Appl. No.: 14/486,275

(22) Filed: Sep. 15, 2014

(65) Prior Publication Data

US 2015/0039346 A1 Feb. 5, 2015

Related U.S. Application Data

(63) Continuation of application No. 13/298,635, filed on Nov. 17, 2011, now Pat. No. 8,838,565.

(51) Int. Cl.
*G06F 17/30* (2006.01)
*G06F 19/00* (2011.01)
(52) U.S. Cl.
CPC .... *G06F 19/3443* (2013.01); *G06F 17/30244* (2013.01); *G06F 17/30386* (2013.01);
(Continued)

(58) Field of Classification Search
CPC ..................................................... G06F 19/322
See application file for complete search history.

(56) References Cited

U.S. PATENT DOCUMENTS

2005/0144042 A1   6/2005  Joffe
2009/0119330 A1   5/2009  Sampath
(Continued)

OTHER PUBLICATIONS

Ozyurt et al. (Federated Web-accessible Clinical Data management within an Extensible NeuroImaging Database; Neuroinform (2010) 8:231-249; Published online: Jun. 22, 2010.
(Continued)

*Primary Examiner* — Syed Hasan
(74) *Attorney, Agent, or Firm* — Hunton & Williams LLP

(57) ABSTRACT

Systems for and methods of utilizing a neuroimaging database are presented. The systems and methods include techniques for analyzing the pathophysiological basis of a chronic brain disease and/or the effectiveness of a treatment for a chronic brain disease, obtaining data for research of a chronic brain disease, searching for chronic brain disease symptoms identified in a clinical patient, searching a database by comparing the brain scan images of patients with suspected indications of chronic brain disease with other patients in the database to identify sets of patients with similar indications in their brain scan images, displaying brain scan information regarding a person, and using image pattern matching to analyze the pathophysiological basis of a chronic brain disease and/or the effectiveness of a proposed or previously administered treatment for a chronic brain disease.

34 Claims, 19 Drawing Sheets

(52) U.S. Cl.
CPC .......... *G06F 19/321* (2013.01); *G06F 19/322* (2013.01); *G06F 19/345* (2013.01)

(56) References Cited

U.S. PATENT DOCUMENTS

| | | | |
|---|---|---|---|
| 2009/0180693 A1 | 7/2009 | Desai et al. | |
| 2009/0253982 A1* | 10/2009 | Wang .................... | A61B 5/055 600/419 |
| 2011/0264461 A1 | 10/2011 | Benja-Athon | |
| 2012/0135935 A1* | 5/2012 | Eisenbach-Schwartz | A61K 38/22 514/17.6 |

OTHER PUBLICATIONS

International Search Report with Written Report from PCT/US2012/65926; May 15, 2013.

* cited by examiner

Normal vs. Anxiety Disorder

Normal vs. Alzheimer's

Oasis

Baseline Data normalized to Cerebellar Maximum
Comparing to Elderly Normals II
Population Information:
24 subjects
Age: from 46 to 99
Clinical Group: Standard Normal
Voxel Data: Relative
Normalization: To Cerebellum Max

3D Voxel ROI Comparison

| Roi Labels | # Elts | Volume (mL) | Max (s.d.) | Min (s.d.) | Mean (s.d.) | SD (s.d.) |
|---|---|---|---|---|---|---|
| OASIS_Anterior Cerebral-Left | 34,471.00 | 128.37 | 3.36 | -5.00 | -2.41 | -3.61 |
| OASIS_Anterior Cerebral-Right | 34,471.00 | 128.37 | 4.36 | -5.00 | -2.40 | -3.71 |
| OASIS_Middle Cerebral-Left | 76,857.00 | 286.21 | 4.62 | -5.00 | -2.28 | -3.48 |
| OASIS_Middle Cerebral-Right | 76,857.00 | 286.21 | 3.95 | -5.00 | -2.19 | -3.46 |
| OASIS_Vertebral Terrain-Left | 29,040.00 | 108.14 | 4.46 | -5.00 | -1.57 | -3.42 |
| OASIS_Vertebral Terrain-Right | 29,040.00 | 108.14 | 3.64 | -5.00 | -1.28 | -3.26 |
| OASIS_Area 4-Left | 4,972.00 | 18.52 | 1.21 | -5.00 | -3.37 | -3.93 |
| OASIS_Area 4-Right | 4,972.00 | 18.52 | 0.73 | -5.00 | -3.30 | -3.86 |
| OASIS_Area 5-Left | 1,305.00 | 4.86 | -0.75 | -5.00 | -2.53 | -3.87 |
| OASIS_Area 5-Right | 1,305.00 | 4.86 | -0.88 | -4.97 | -2.47 | -4.08 |
| OASIS_Area 6-Left | 7,966.00 | 29.66 | -0.20 | -5.00 | -3.30 | -4.09 |
| OASIS_Area 6-Right | 7,966.00 | 29.66 | 0.73 | -5.00 | -3.21 | -3.91 |
| OASIS_Area 7-Left | 7,526.00 | 28.03 | 1.79 | -5.00 | -1.62 | -3.82 |
| OASIS_Area 7-Right | 7,526.00 | 28.03 | 0.93 | -5.00 | -1.85 | -3.76 |
| OASIS_Area 8-Left | 4,613.00 | 17.18 | 1.14 | -4.97 | -2.29 | -4.00 |
| OASIS_Area 8-Right | 4,613.00 | 17.18 | 0.60 | -5.00 | -2.41 | -3.90 |

Fig. 15A

| Roi Labels | # Elts | Volume (mL) | Max (s.d.) | Min (s.d.) | Mean (s.d.) | SD (s.d.) |
|---|---|---|---|---|---|---|
| OASIS_Area 9-Left | 4,216.00 | 15.70 | 2.78 | -4.97 | -1.55 | -3.74 |
| OASIS_Area 9-Right | 4,216.00 | 15.70 | 2.53 | -5.00 | -1.69 | -3.55 |
| OASIS_Area 10-Left | 5,689.00 | 21.19 | 4.99 | -5.00 | -1.40 | -3.24 |
| OASIS_Area 10-Right | 5,689.00 | 21.19 | 4.36 | -5.00 | -1.38 | -3.19 |
| OASIS_Area 11-Left | 2,576.00 | 9.59 | 1.25 | -5.00 | -1.38 | -4.10 |
| OASIS_Area 11-Right | 2,576.00 | 9.59 | 0.93 | -4.98 | -1.46 | -4.01 |
| OASIS_Area 17-Left | 2,487.00 | 9.26 | 1.16 | -4.96 | -1.86 | -3.96 |
| OASIS_Area 17-Right | 2,487.00 | 9.26 | 3.05 | -5.00 | -0.59 | -3.53 |
| OASIS_Area 18-Left | 5,062.00 | 18.85 | 3.29 | -5.00 | -1.30 | -3.54 |
| OASIS_Area 18-Right | 5,062.00 | 18.85 | 3.48 | -5.00 | -0.71 | -3.29 |
| OASIS_Area 19-Left | 4,669.00 | 17.39 | 2.84 | -4.97 | -0.75 | -3.86 |
| OASIS_Area 19-Right | 4,669.00 | 17.39 | 2.63 | -4.98 | -0.21 | -3.84 |
| OASIS_Area 20-Left | 3,132.00 | 11.66 | 0.24 | -5.00 | -2.58 | -3.84 |
| OASIS_Area 20-Right | 3,132.00 | 11.66 | -0.44 | -5.00 | -2.82 | -3.80 |
| OASIS_Area 21-Left | 4,951.00 | 18.44 | -1.07 | -5.00 | -3.72 | -4.17 |
| OASIS_Area 21-Right | 4,951.00 | 18.44 | 1.59 | -5.00 | -3.65 | -3.73 |
| OASIS_Area 22-Left | 3,794.00 | 14.13 | 0.09 | -4.96 | -2.77 | -4.10 |
| OASIS_Area 22-Right | 3,794.00 | 14.13 | 1.33 | -5.00 | -2.33 | -3.90 |
| OASIS_Area 23-Left | 3,122.00 | 11.63 | 0.47 | -5.00 | -3.61 | -3.82 |
| OASIS_Area 23-Right | 3,122.00 | 11.63 | 0.65 | -5.00 | -3.13 | -3.83 |
| OASIS_Area 24-Left | 3,891.00 | 14.49 | 1.22 | -5.00 | -2.83 | -3.85 |
| OASIS_Area 24-Right | 3,891.00 | 14.49 | 0.47 | -5.00 | -2.75 | -4.10 |
| OASIS_Area 25-Left | 448.00 | 1.67 | 0.79 | -4.97 | -1.37 | -4.30 |
| OASIS_Area 25-Right | 448.00 | 1.67 | -0.46 | -4.98 | -2.18 | -4.21 |
| OASIS_Area 28-Left | 876.00 | 3.26 | 0.08 | -4.98 | -2.15 | -4.07 |
| OASIS_Area 28-Right | 876.00 | 3.26 | -0.37 | -5.00 | -2.86 | -4.05 |
| OASIS_Area 31-Left | 2,814.00 | 10.48 | 0.72 | -4.97 | -2.14 | -3.90 |
| OASIS_Area 31-Right | 2,814.00 | 10.48 | 0.79 | -5.00 | -1.94 | -3.64 | fig. 15B

| Roi Labels | # Elts | Volume (mL) | Max (s.d.) | Min (s.d.) | Mean (s.d.) | SD (s.d.) |
|---|---|---|---|---|---|---|
| OASIS_Area 32-Left | 3,945.00 | 14.69 | 0.21 | -5.00 | -2.90 | -3.92 |
| OASIS_Area 32-Right | 3,945.00 | 14.69 | 0.41 | -5.00 | -2.15 | -4.18 |
| OASIS_Area 36-Left | 1,368.00 | 5.09 | 0.39 | -5.00 | -1.76 | -4.06 |
| OASIS_Area 36-Right | 1,368.00 | 5.09 | 0.46 | -5.00 | -2.36 | -3.84 |
| OASIS_Area 37-Left | 3,081.00 | 11.47 | 1.41 | -5.00 | -1.53 | -3.66 |
| OASIS_Area 37-Right | 3,081.00 | 11.47 | 2.69 | -5.00 | -1.62 | -3.42 |
| OASIS_Area 38-Left | 1,343.00 | 5.00 | -0.41 | -4.71 | -2.43 | -4.24 |
| OASIS_Area 38-Right | 1,343.00 | 5.00 | -0.70 | -5.00 | -2.60 | -4.22 |
| OASIS_Area 39-Left | 1,565.00 | 5.83 | 0.76 | -4.97 | -1.51 | -4.01 |
| OASIS_Area 39-Right | 1,565.00 | 5.83 | 2.73 | -5.00 | -0.89 | -3.36 |
| OASIS_Area 40-Left | 3,623.00 | 13.49 | 0.48 | -5.00 | -2.21 | -3.75 |
| OASIS_Area 40-Right | 3,623.00 | 13.49 | 1.32 | -5.00 | -1.88 | -3.57 |
| OASIS_Area 44-Left | 1,260.00 | 4.69 | 0.05 | -4.43 | -2.27 | -4.16 |
| OASIS_Area 44-Right | 1,260.00 | 4.69 | 1.02 | -4.29 | -1.97 | -4.11 |
| OASIS_Area 45-Left | 2,011.00 | 7.49 | 1.02 | -4.69 | -1.77 | -4.08 |
| OASIS_Area 45-Right | 2,011.00 | 7.49 | 1.26 | -4.81 | -1.91 | -3.79 |
| OASIS_Area 46-Left | 1,854.00 | 6.90 | 1.07 | -5.00 | -2.21 | -3.66 |
| OASIS_Area 46-Right | 1,854.00 | 6.90 | 2.57 | -4.72 | -1.71 | -3.28 |
| OASIS_Area 47-Left | 2,138.00 | 7.96 | -0.47 | -5.00 | -2.87 | -4.03 |
| OASIS_Area 47-Right | 2,138.00 | 7.96 | -0.09 | -4.97 | -2.18 | -4.21 |
| OASIS_Cerebral Cortex-Left | 127,354.00 | 474.25 | 4.99 | -5.00 | -2.09 | -3.49 |
| OASIS_Cerebral Cortex-Right | 127,354.00 | 474.25 | 5.00 | -5.00 | -1.87 | -3.32 |
| OASIS_Frontal Lobe-Left | 59,798.00 | 222.68 | 3.36 | -5.00 | -2.43 | -3.62 |
| OASIS_Frontal Lobe-Right | 59,798.00 | 222.68 | 4.36 | -5.00 | -2.25 | -3.53 |
| OASIS_Occipital Lobe-Left | 12,482.00 | 46.48 | 3.12 | -5.00 | -1.33 | -3.73 |
| OASIS_Occipital Lobe-Right | 12,482.00 | 46.48 | 3.15 | -5.00 | -0.64 | -3.53 |
| OASIS_Parietal Lobe-Left | 25,766.00 | 95.95 | 1.79 | -5.00 | -2.11 | -3.69 |

Fig. 15C

| Roi Labels | # Elts | Volume (mL) | Max (s.d.) | Min (s.d.) | Mean (s.d.) | SD (s.d.) |
|---|---|---|---|---|---|---|
| OASIS_Parietal Lobe-Right | 25,766.00 | 95.95 | 3.15 | -5.00 | -1.95 | -3.56 |
| OASIS_Temporal Lobe-Left | 20,953.00 | 78.03 | 1.41 | -5.00 | -2.84 | -3.76 |
| OASIS_Temporal Lobe-Right | 20,953.00 | 78.03 | 3.25 | -5.00 | -2.86 | -3.67 |
| OASIS_Cerebellum-Left | 14,470.00 | 53.88 | 2.89 | -5.00 | -1.41 | -3.50 |
| OASIS_Cerebellum-Right | 14,470.00 | 53.88 | 3.74 | -5.00 | -1.31 | -3.51 |
| OASIS_Caudate Nucleus-Left | 975.00 | 3.63 | 3.56 | -5.00 | -0.02 | -3.42 |
| OASIS_Caudate Nucleus-Right | 975.00 | 3.63 | 3.86 | -4.36 | -0.63 | -3.58 |
| OASIS_Putamen-Left | 1,668.00 | 6.21 | 4.62 | -5.00 | -0.34 | -3.30 |
| OASIS_Putamen-Right | 1,668.00 | 6.21 | 2.44 | -4.90 | -1.05 | -3.44 |
| OASIS_Thalamus-Left | 1,487.00 | 5.54 | 4.65 | -1.03 | 1.63 | -3.87 |
| OASIS_Thalamus-Right | 1,487.00 | 5.54 | 4.54 | -1.08 | 1.79 | -4.00 |

Fig. 15D

Example: Preliminary analysis of patients under 18 years old at time of scan showing comorbidity and overlapping diagnoses.

Number of scanned patients < 18: 374
As of: 10/7/2011

| Reason for Scan | # | % of scanned group % | Pts. with a history of hypoxia (birth trauma) # | Incoming Dx From referring provider | | | | Outgoing Dx by interpreting physician | | |
|---|---|---|---|---|---|---|---|---|---|---|
| | | | | None # | ADHD # | Bipolar # | Brain injury, concussion # | Attention Deficit # | Bipolar # | Brain injury # |
| ADD | 33 | 9% | 2 | 9 | 12 | 4 | 1 | 15 | 25 | 24 |
| ADHD | 55 | 15% | 8 | 4 | 40 | 0 | 1 | 22 | 48 | 48 |
| Attention (other) | 6 | 2% | 0 | 3 | 2 | 0 | 0 | 3 | 6 | 6 |
| Bipolar | 25 | 7% | 1 | 2 | 15 | 14 | 0 | 16 | 20 | 21 |
| Brain Injury | 21 | 6% | 2 | 1 | 12 | 5 | 5 | 8 | 18 | 16 |
| Concussion | 2 | 1% | 0 | 0 | 0 | 0 | 1 | 1 | 1 | 2 |

Note: Columns are not additive because some patients are in multiple categories due to comorbid conditions.

Preliminary Observations by Dr. Smith after reviewing the data:
  Many of the cases are unrecognized illness based only on the clinical exam.
  2/3 of cases presenting with complicated ADHD actually have bipolar or brain injury implications.
  4/5 of cases presenting with bipolar have a brain injury implication.
  TBI often complicates treatment since it is often diffuse and not easily identified.

Fig. 16

NEUROIMAGING DATABASE SYSTEMS AND METHODS

CROSS-REFERENCE TO RELATED APPLICATIONS

This patent application is a Continuation of U.S. patent application Ser. No. 13/298,635 filed Nov. 17, 2011, which is hereby incorporated by reference herein in its entirety.

FIELD OF THE INVENTION

The present invention relates to systems and methods of utilizing neuroimaging databases.

BACKGROUND OF THE INVENTION

Neuroimaging studies of a patient's brain, such as those obtained using single Photon Emission Computed Tomography (SPECT) or Functional Magnetic Resonance Imaging (fMRI), are often used in the diagnosis, treatment, and study of chronic brain diseases. As just some examples, a physician may perform a brain scan to determine a diagnosis for a patient that suffered a serious head injury, to prepare a treatment plan for a patient with Alzheimer's disease, or to assess whether a particular pharmaceutical is helping a patient who has bipolar disorder.

Clinical Decision Support Systems (CDSS) have become increasingly popular among physicians and other health care professionals recently. In general, CDSS may refer to computer hardware, software, and/or systems that can be used to provide clinicians, staff, patients, or other individuals with knowledge and person-specific information, intelligently filtered or presented at appropriate times, to enhance health and health care. For example, a physician may use CDSS to determine a diagnosis for a patient who has certain symptoms. CDSS often include at least three component parts: a knowledge basis, an inference engine, and a communication mechanism. The knowledge base may comprise compiled information about symptoms, pharmaceuticals, and other medical information. The inference engine may comprise formulas, algorithms, etc. for combining information in the knowledge base with actual patient data. The communication mechanism may be ways to input patient data and to output helpful information based on the knowledge base and inference engine. For example, information may be inputted by a physician using a computer keyboard or tablet and displayed to the physician on a computer monitor or portable device.

SUMMARY OF THE INVENTION

Various exemplary embodiments provide for ways of utilizing neuroimaging databases.

Brain scans may provide a wealth of information regarding the various portions of the brain down to a very fine detail. When diagnosing, treating, and studying chronic brain diseases, it may be desirable to compare in various ways a patient's brain scan(s) with those of other patients, including those considered normal, those with similar conditions, and those receiving similar treatments, for example. It may also be desirable to compare functional images of a patient's brain while the patient is at rest, versus while the patient is concentrating and his or her brain is activated.

In one illustrative example, a system and method may be provided for analyzing the pathophysiological basis of a chronic brain disease and/or the effectiveness of a certain treatment for a chronic brain disease. A database may contain a set of records for patients that received particular treatments for a chronic brain disease, as well as a set of records for patients that did not receive the treatments. A normative database may contain information, such as brain scans, for patients with normal brain scans. Through the analysis of statistical comparisons of (1) the treatment set to the normative set, and (2) the non-treatment set to the normative set, it may be possible to learn more about the chronic brain disease and/or analyze the effectiveness of the treatment.

In another illustrative example, pattern matching may be used. A database may contain perfusion pattern index (PPI) files for individual patients, where a PPI file may show statistical deviations of the brain perfusion levels in the regions of a patient's brain from a set of normative values for patients with no indications of chronic brain disease. One patient's PPI file may be compared to other patients to obtain a set of similar patients, an average PPI file may be determined for the set, and the PPI file of each patient may then be compared to the average PPI file. Such comparison information may also be useful to learn more about a chronic brain disease and/or analyze the effectiveness of a treatment.

Other embodiments are also within the scope of the invention.

BRIEF DESCRIPTION OF THE DRAWINGS

The present invention, together with further objects and advantages, may best be understood by reference to the following description taken in conjunction with the accompanying drawings, in the several figures of which like reference numerals identify like elements, and in which:

FIG. 8 is a general information and history page according to an embodiment of the present invention;

FIG. 9 is a scan encounter page according to an embodiment of the present invention;

FIGS. 15A-D are a table for use in an embodiment of the present invention; and

FIG. 16 is a portion of an example patient analysis report according to an embodiment of the present invention.

DETAILED DESCRIPTION OF PREFERRED EMBODIMENTS

The following description is intended to convey a thorough understanding of the embodiments described by providing a number of specific embodiments and details involving systems and methods of utilizing brain scan databases. It should be appreciated, however, that the present disclosure is not limited to these specific embodiments and details, which are exemplary only. It is further understood that one possessing ordinary skill in the art, in light of known systems and methods, would appreciate the use of the invention for its intended purposes and benefits in any number of alternative embodiments, depending on specific design and other needs.

Disclosed herein are systems and methods of utilizing brain scan databases. According to certain embodiments, techniques for analyzing the pathophysiological basis of chronic brain diseases and/or the effectiveness of a proposed or previously administered treatment for a chronic brain disease are disclosed. According to other embodiments, techniques for obtaining data for research of a chronic brain disease are disclosed. According to other embodiments, techniques for searching for chronic brain disease symptoms identified in a clinical patient are disclosed. According to yet other embodiments, techniques for displaying brain scan information regarding a person are disclosed. According to yet other embodiments, techniques for using pattern matching to analyze the pathophysiological basis of a chronic brain disease and/or the effectiveness of a proposed or previously administered treatment for a chronic brain disease are disclosed.

Figure 1:
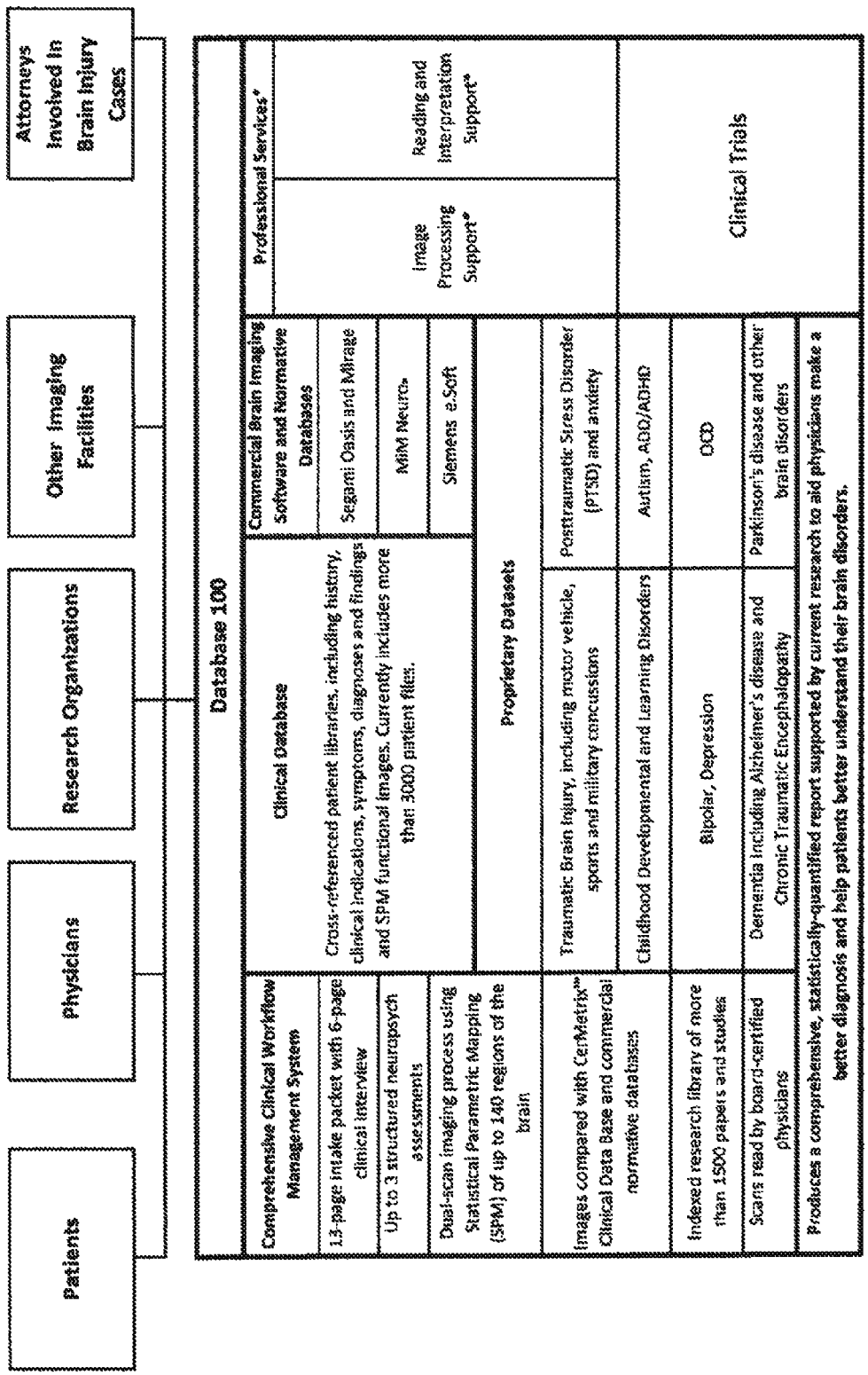
FIG. 1 is a schematic diagram illustrating a system according to an embodiment of the present invention.

FIG. 1 is a schematic diagram illustrating a system according to an embodiment of the present invention. In particular, FIG. 1 illustrates a database 100, which includes a plurality of electronically-stored records (e.g., 1000, 2500, 5000, 7500, 10,000, or more). As discussed in detail below, each record corresponds to a person and contains detailed information regarding that person.

Each record in database 100 includes at least one, and typically more, functional neuroimaging brain scans. For example, such brain scans may be obtained using Single Photon Emission Computed Tomography (SPECT) cameras. In this embodiment, a radiopharmaceutical, such at GE Healthcare's Ceretec®, containing a small amount of a radioactive isotope tracer may be injected into the patient's arm. The radiopharmaceutical is carried by the blood to the patient's brain, crosses the blood-brain barrier, and is diffused into various regions throughout the brain. The tracer emits gamma radiation, which passes out of the patient's head and is captured by one or more detectors in the SPECT camera. The number of gamma rays counted by the camera may be directly indicative of the intensity of the tracer uptake and neuronal function in various regions of the brain. The resulting brain scans may be stored as data structures that define a set of numeric representations of three dimensional voxels (i.e., volumetric pixels) where the x, y, and z axis represent a specific volumetric area of the brain. The camera and its software may translate these three dimensional voxels into a set of transverse planes where each plane is a two-dimensional matrix reflecting a particular slice or section of the patient's brain. The intensity of the image in each cell in the matrix may represent the level of uptake of the tracer in that part of the brain. Using Digital Imaging and Communications in Medicine (DICOM) image readers available from various sources (e.g., Siemens eSoft), each matrix may be viewed in grey scale or rendered into multicolored images where different levels of intensity are represented by different colors. In various exemplary embodiments, each stored scan may contain data representing several optional scan settings, such as thirty-two planes (or slices), each plane consisting of 64×64 voxels; or sixty-four planes (or slices), each plane consisting of 128×128 voxels; or 128 planes (or slices), each plane consisting of 256×256 voxels. Values for each voxel may be stored in database 100, and each value may represent data from the raw images coming directly from the camera, or the data may reflect a difference from norm. That is, database 100 may store a set of values representing brain scan voxels, where each value represents a delta from what a normal brain scan should be for that voxel, as determined by comparison with one or more normative databases.

Scans may be obtained with a variety of medical imaging devices, such as, for example, a Siemens E-Cam SPECT camera with low-energy, high resolution (LEHR) parallel hole collimation. In an exemplary embodiment, counts may be collected in a 64×64 matrix with 32 stops of three degrees each. Total counts may exceed five million. Data may be zoomed to 1.78, corrected for motion artifact, and filtered using a Butterworth filter at 0.60 with an order of six. Attenuation correction may be performed. The volume may be masked to exclude non-neural structures. There may be no post filtering, or post filtering may be performed. Data may be presented and stored in horizontal, sagittal, and frontal views with, for example, four millimeter sections. Statistical parametric analysis may be performed using various image interpretation software packages, such as, for example, Segami Corporation NeuroSPECT software relative to a normative database containing information for any number of individuals (e.g., 64). A computer-implemented tomographic reconstruction algorithm may be applied to the multiple projections obtained from the scan, yielding a three dimensional dataset, which may then be manipulated to show thin slices along any chosen axis. Again, while the previous example described a particular type of SPECT functional brain scan, any type of neuroimaging study, and any combination of neuroimaging modalities (e.g., PET scan and fMRI scan), may be used to populate the database.

Each brain scan may undergo a spatial normalization process for storage in database 100. Such a process may include any, or a combination, of translation, rotation, scaling, and nonlinear warping of the brain surface. Spatial normalization allows for the gathered data to conform to a standard template. Exemplary templates include Talairach-Tournoux and those available from the Montreal Neurological Institute.

Data from each scan may be stored using, by way of non-limiting example, Cartesian coordinates or Talairach coordinates. An exemplary non-limiting example image set may include raw DICOM files showing scans of the patient's brain in multiple planes, one or more sets of processed DICOM images (for detailed resolution and clarity), and focused image sets in PNG or JPG formats, highlighting parts of the patient's brain that show specific functional abnormalities. (The DICOM standard is also known as NEMA standard PS3 and ISO standard 12052: 2006.)

Each record in database 100 may include a brain scan representing an at-rest state, also known as a baseline state, which may be gathered as follows. The subject may be placed in a comfortable reclining chair, and an intravenous line may be started. The subject may then be allowed to acclimate to a quiet semi-darkened room with sound-dampening headphones in place, according to established practice guidelines. A 99mTc-labeled Tc-Hexamethylpropyleneamine Oxime (HMPAO, also known as exametazime) tracer may then be injected through the intravenous line, and the intravenous line may be flushed with saline. Other types of radiopharmaceutical tracers may be used as well (e.g., 123I IMP tracer, 99mTc ECD tracer). The perfusion pattern of the subject's brain may then become fixed physiologically in the patient's brain during the subsequent three minutes. After injection, the subject may remain in the quiet semi-darkened room for an additional period. Scans may be acquired forty minutes after tracer injection.

Each record in database 100 may include a functional brain scan representing an active state, which may be gathered as follows. For a concentration task, the subject may be placed in a quiet room and an intravenous line may be started. The subject may then perform a concentration test, such as, by way of non-limiting example, a Stroop colored word test on a laptop computer. Approximately five minutes into the concentration test, the 99mTc-labeled HMPAO tracer may be injected through the intravenous line, and the intravenous line may be flushed with saline. The subject may complete the concentration test, and forty minutes after injection, the patient may be scanned.

Brain scans in database 100 may be obtained from patients or other subjects, obtained from third parties (e.g., scanned by business partners, purchased from vendors), or a combination thereof.

Each record in database 100 further may include detailed data on any, or a combination, of a clinical history, a family history, presenting symptoms, a doctor's diagnosis, medications, previous treatments, a referring physician's reasons for ordering the scan, military service, and any current and previous substance or alcohol abuse history. The clinical history may contain information on any, or a combination, of developmental history (including information about childhood and adolescent developmental traumas), specific brain trauma (e.g., from accidents, sports, toxic exposure), surgeries and hospitalizations, other imaging procedures completed (including copies of such images), medical and environmental allergies, and family members' conditions, diseases, and disorders. Each record may further include a written report correlating specific scan images with potential conditions and disorders. Each record may further include one or more structured neuropsychiatric inventories, such as, by way of non-limiting example, a Mini International Neuropsychiatric Interview (MINI) and a Montreal Cognitive Assessment (MoCA). Each record may include a report by one or more radiologists or physicians trained to interpret the brain scans indicating the radiologists' and/or physicians' findings, interpretations, and recommendations. The data referred to in this paragraph may be stored in any of a variety of formats such as, by way of non-limiting example, ASCII, MICROSOFT WORD, and Portable Document Format (PDF), or contained within the data fields of software programs such as Microsoft Customer Relationship Management (CRM).

Collectively, the data in a record in database 100 for a particular patient that may reflect or refer to the patient's medical state at any time may be referred to as "patient medical information." Patient medical information may include, by way of non-limiting example, clinical history, family history, presenting symptoms, a doctor's diagnosis, medications, previous treatments, military service, and any current and previous substance or alcohol abuse history.

In certain embodiments, database 100 may include records for patients diagnosed with, by way of non-limiting example, traumatic brain injury, Alzheimer's disease, dementia, bipolar disorder, attention deficit hyperactivity disorder (ADHD), anxiety, autism and other brain conditions and disorders.

Database 100 may be implemented in various ways. By way of non-limiting example, database 100 may be built on a Structured Query Language (SQL) platform and accessed through a Microsoft Dynamics Customer Relationship Management (CRM) front-end. The CRM may be structured as an electronic health record (EHR), electronic medical record (EMR), clinical data repository, or patient registry. Database 100 may capitalize on the inherent capabilities of the CRM platform to organize and automate many corporate and clinical processes into an integrated, computer-aided management system. This may include marketing and sales functions related to acquiring new referring attorneys and physicians, as well as tracking patient acquisition and booking. It may also integrate billing and accounting functions, such as by tracking the progress of patients through various steps and capturing cost and revenue data.

Database 100 (and associated systems and infrastructure) may be configured to comply with U.S. and international standards, such as HL-7, ISO TC/251 and DICOM, European standards such as CEN, and the applicable U.S. regulations for Health Insurance Portability and Accountability (HIPAA), 21 C.F.R. Part 11, Health Information Technology for Economic and Clinical Health (HITECH), and similar statutes. Data may be stored in unstructured (e.g., natural language) form or encoded using standard healthcare industry standards such as ICD-9/10, SNOMED-CT, RxNorm, or LOINC. Data entry may be performed using a variety of techniques, such as direct entry by keyboard, tablet or touchpad, screen capture, speech recognition, file transfers, or imported from other systems and software.

Database 100 may be accessed by various entities. Examples of such entities include patients, physicians, research organizations, imaging companies, and attorneys involved in brain injury cases. Such entities may retrieve data from the database, and, in some cases, add data to the database. Access to database 100 may be provided over secure, high-speed Internet connections using, by way of non-limiting example, high performance WAN optimization software licensed from Circadence Corporation. The DICOM communications protocol may be used.

The database and access arrangements may be implemented using appropriate privacy and security measures, such as user authentication and authorization, passwords, data-de-identification, encryption, and access control methodologies to insure compliance with all federal and state requirements. Servers and access control devices may be maintained in secure computing and hosting facilities to assure compliance with HIPAA and other laws and regulations.

Figure 2:
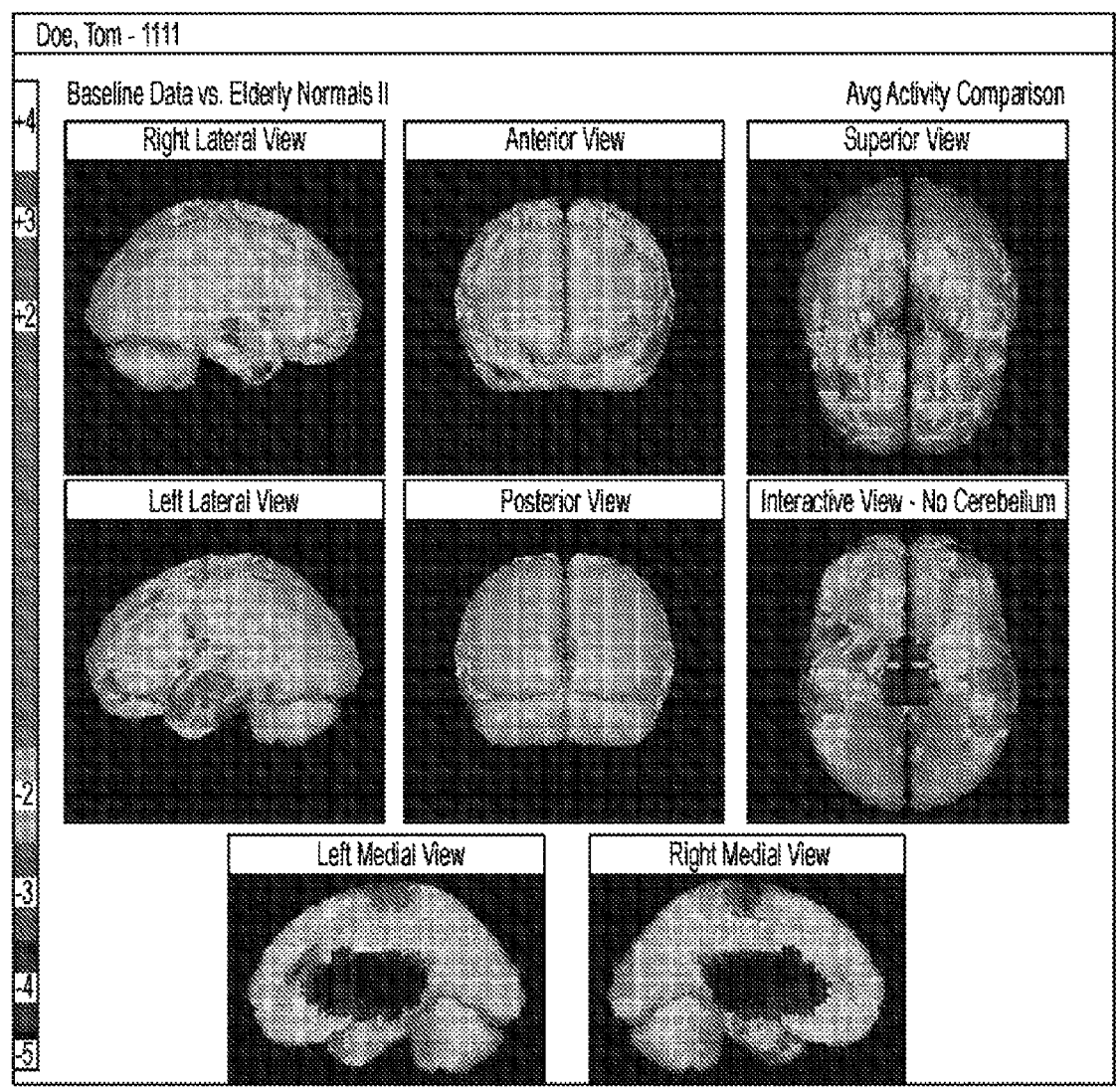
FIG. 2 is a portion of an example assessment report according to an embodiment of the present invention.

Certain embodiments of the present invention may also include, or include access to, a normative database. The normative database may be a portion of database 100. Alternately, or in addition, the normative database may be a physically or logically separate database. The normative database may include data associated with patients with normal brain scans. Thus, the normative database may include records of a plurality of clinical patients. Each record may include at least one, and potentially more, brain scans. Both baseline and concentration brain scans may be included. FIG. 2 is a portion of an example assessment report according to an embodiment of the present invention.

In particular, FIG. 2 illustrates a three-dimensional Talairach rendering of brain activity. The brain scan data reflected in the image of FIG. 2 is spatially normalized such that it is presented on a standard image of a generic brain. The activity depicted represents deviations from normal for each surface voxel. Because the brain under analysis in FIG. 2 is that of an elderly patient, deviations may be judged with a normal elderly brain activity as a baseline represented by the color grey. Each color in the image of FIG. 2 represents a departure from such a baseline state.

Figure 4:
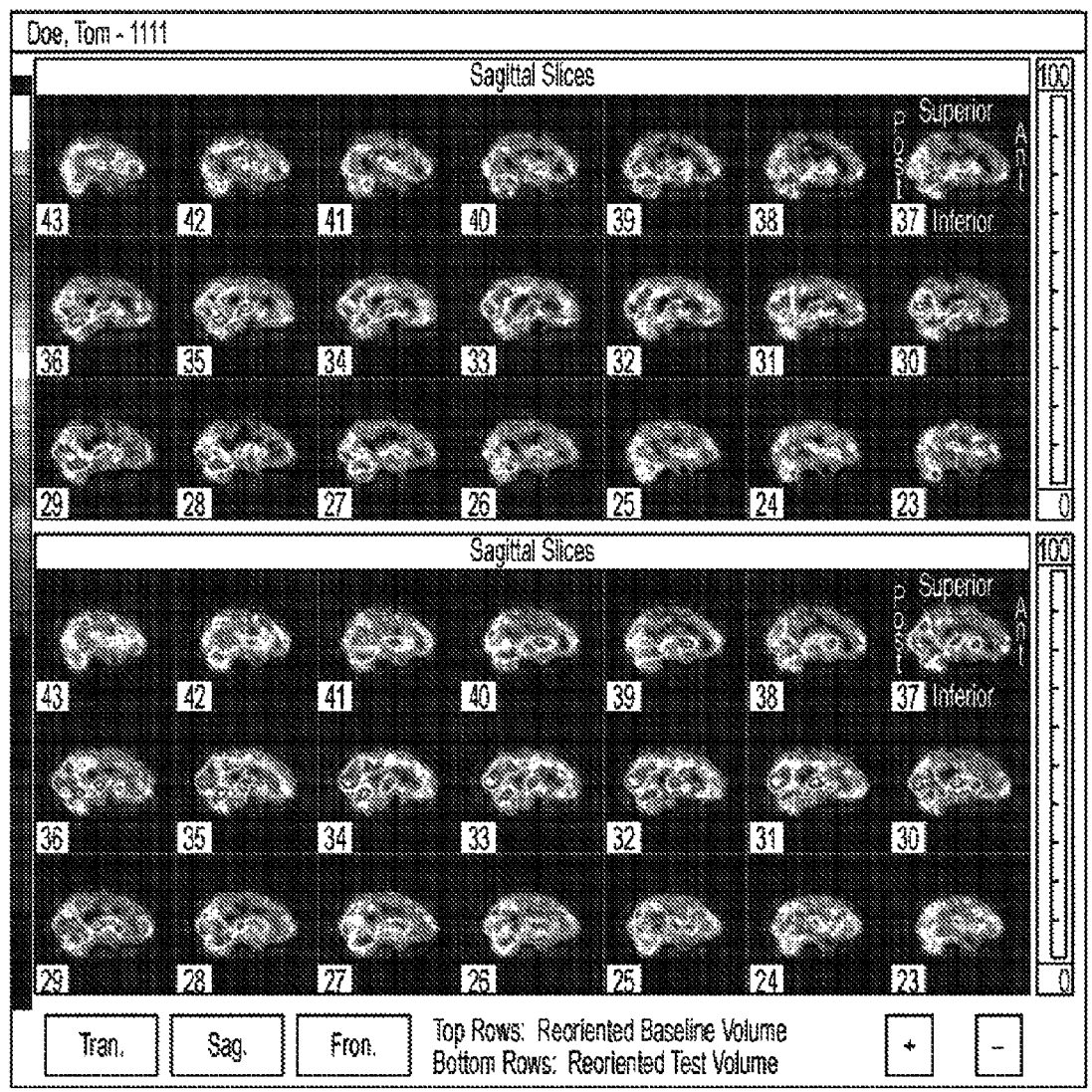
FIG. 4 is a portion of an example assessment report according to an embodiment of the present invention.

In general, brain scan data may be presented in visual form in reports according to embodiments of the present invention according to any of various techniques. Colors may be used with any of these techniques to depict deviations from normal brain activity. Two-dimensional slices of data representing a three-dimensional brain scan may be utilized (FIGS. 4-6). For such slicing techniques, planes may be in any configuration or orientation (e.g., sagittal, coronal, transverse, curved plane). Isosurface rendering may be employed. For volume rendering techniques, direct volume rendering may be implemented (e.g., multi-threshold direct volume rendering). Opacity, color, refractive index, and orientation may be adjusted by users in real time. Other techniques include maximal intensity projections and shaded surface displays (e.g., multi-threshold shaded surface displays). Mesh or grid computational expedients may be employed with any of the aforementioned techniques.

Figure 3:
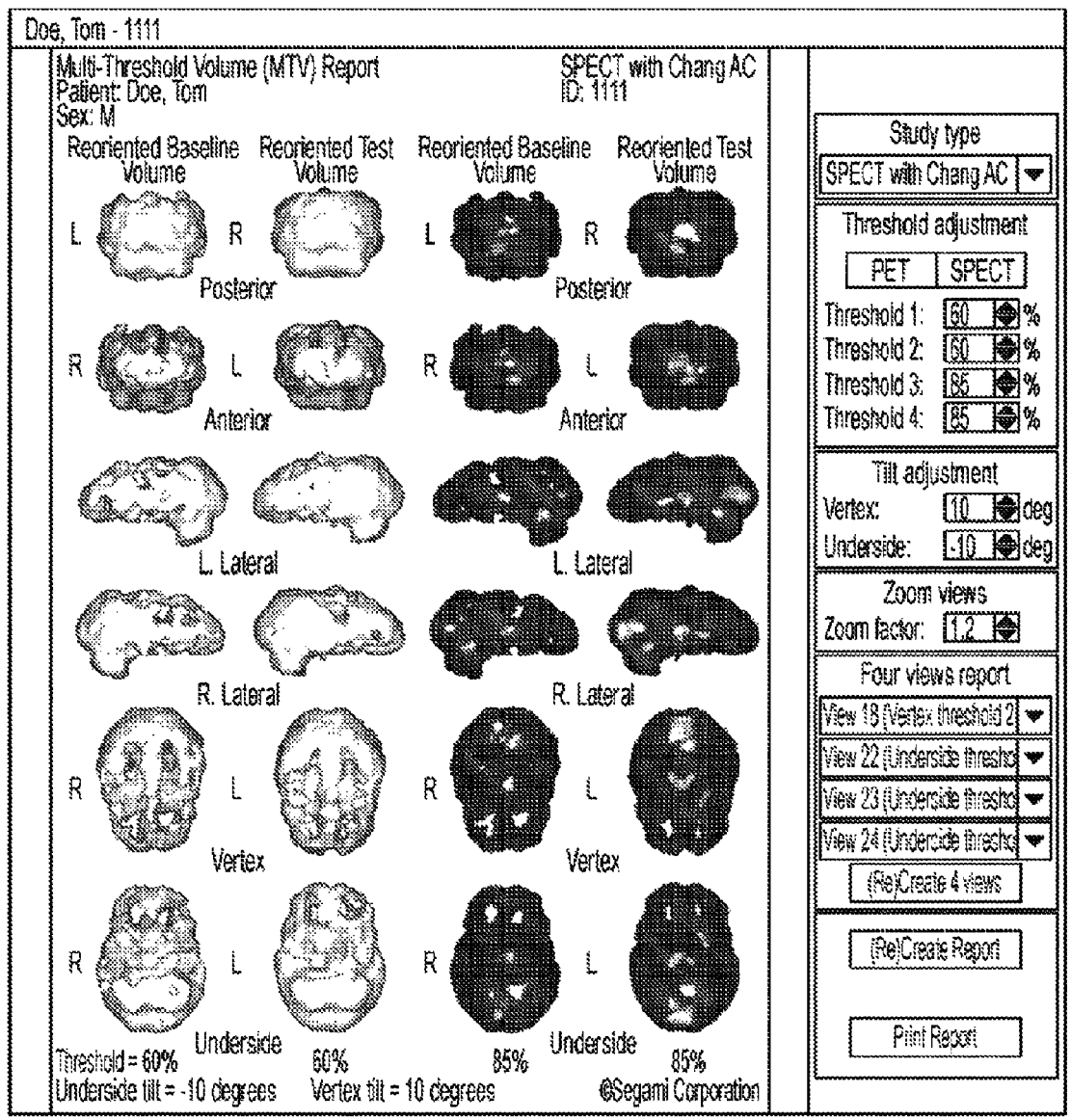
FIG. 3 is a portion of an example assessment report according to an embodiment of the present invention.

FIG. 3 is a portion of an example assessment report according to an embodiment of the present invention. In particular, FIG. 3 depicts multi-threshold volume rendering of brain activity. Both baseline and test (concentration) brain activity are represented. Thresholds of 60% and 85% are depicted in FIG. 3.

FIG. 4 is a portion of an example assessment report according to an embodiment of the present invention. In particular, FIG. 4 depicts sagittal two-dimensional slices of the three-dimensional brain scan data. Activity on both sides of the brain is depicted, where different colors represent deviations from normal activity.

Figure 5A:
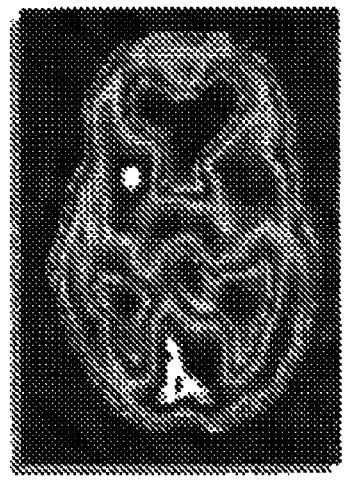
FIG. 5A is a detail of a brain scan according to an embodiment of the present invention.
Figure 6:
FIG. 6 is an example comparison of a normal brain scan versus an anxiety disorder brain scan.
Figure 6:
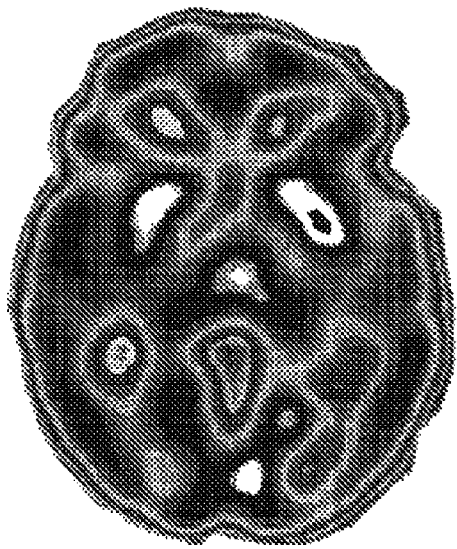

FIG. 5A is a detail of a brain scan according to an embodiment of the present invention. In particular, FIG. 5A depicts a transverse two-dimensional slice of three-dimensional brain scan data. The resolution of the data depicted in FIG. 5A is 64×64 voxels, with a total of 32 planes, of which the plane in FIG. 5A is one.

Figure 5B:
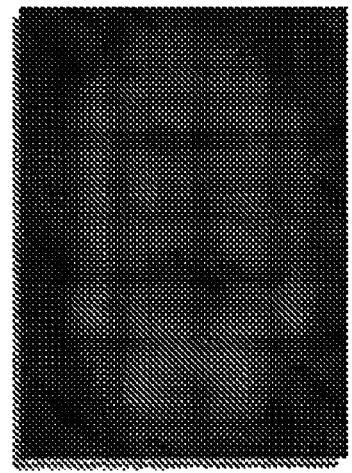
FIG. 5B is a detail of a prior art brain scan.

FIG. 5B is a detail of a prior art brain scan. Prior art brain scans include those of only 32×32×32 voxels. The scan depicted in FIG. 5B is not as detailed as the scan depicted in FIG. 5A.

FIG. 6 is an example comparison of a normal brain scan to an anxiety disorder brain scan. In particular, FIG. 6 depicts transverse two-dimensional slices of three-dimensional brain scan data for a normal brain and a brain of a patient diagnosed with anxiety disorder. Embodiments of the present invention are capable of simultaneously presenting any two comparable (e.g., depicting the same general brain region in the same way) brain images. Such images may be presented on a computer screen. Certain embodiments are capable of generating an image file (e.g., GIF, JPEG, PNG, etc.) containing two or more images, with any (or no) associated written data. Such an image file may be exported from the generating computer system and utilized in a report, demonstration, or other presentation.

Figure 7:
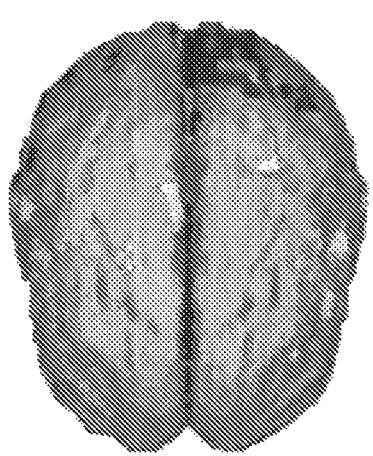
FIG. 7 is an example comparison of a normal brain scan versus an Alzheimer's disease brain scan.
Figure 7:
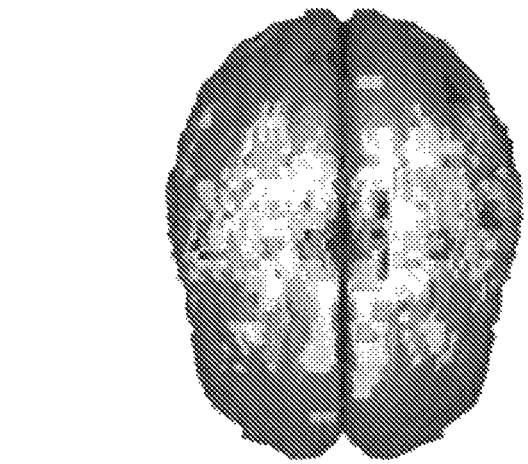

FIG. 7 is an example comparison of a normal brain scan versus an Alzheimer's disease brain scan. In particular, FIG. 7 depicts a Talairach rendering of brain scan data for a normal brain and a brain of a patient diagnosed with Alzheimer's disease. As discussed above in relation to FIG. 6, embodiments of the present invention are capable of simultaneously presenting any two comparable brain images.

Figure 8:
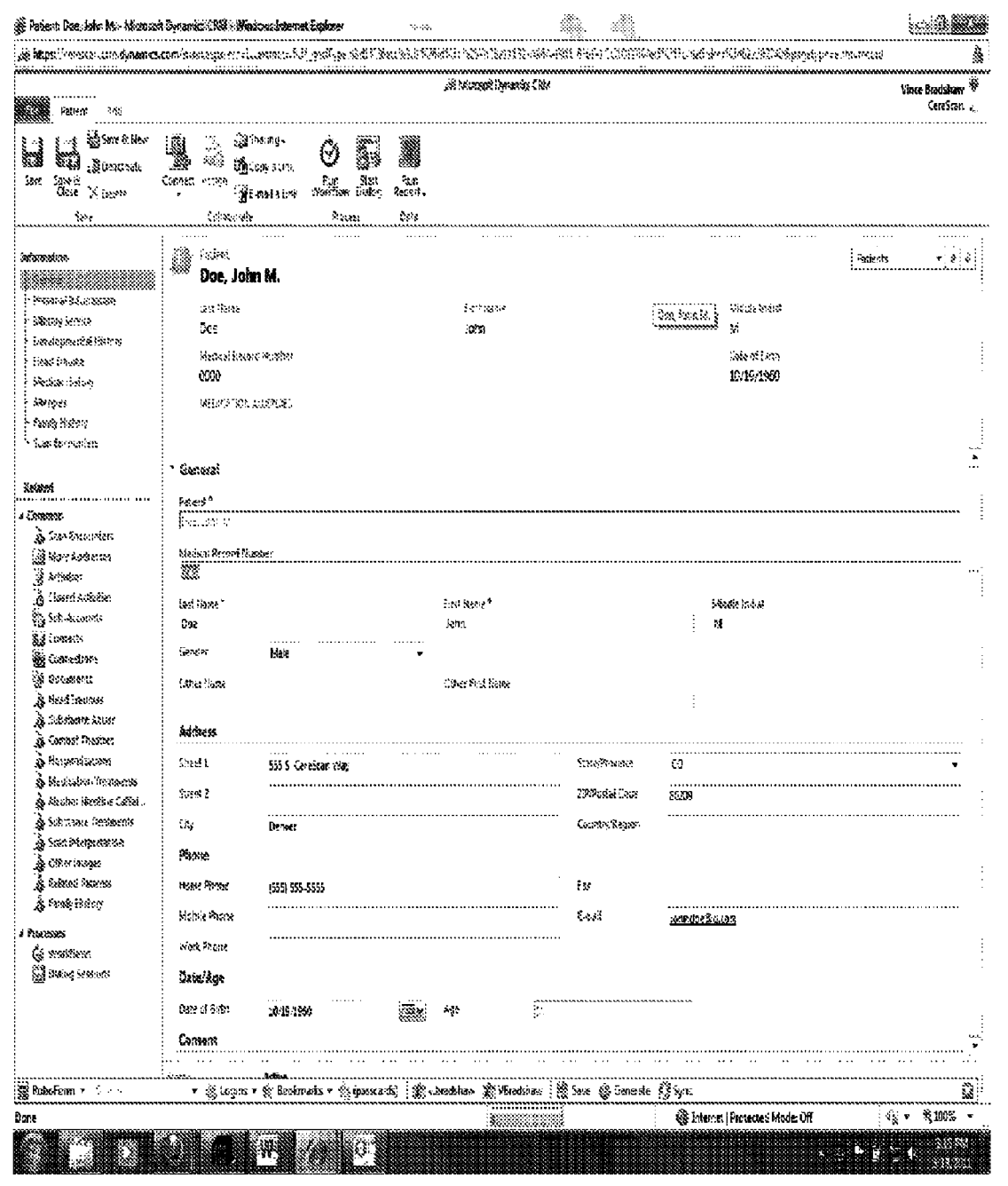

FIG. 8 is a general information and history page according to an embodiment of the present invention. The page may be part of an overall user interface to the database of brain scan information contemplated according to various embodiments of the present invention. Users of the database may enter patient information in an interface page, such as that depicted in FIG. 8, which is displayed on a computer using computer software. That is, FIG. 8 depicts that patient data (e.g., patient demographic data) may be gathered and stored in the overall database. Such information includes, by way of non-limiting example, patient name, gender, address, telephone numbers, and date of birth. The database may also include digital representations of consent forms as executed by patients. Such consent forms may include language providing that patient data may be added to the database and accessed in a manner so as to comply with relevant laws and regulations. For example, the consent forms may specify that patient brain scan data and associated diagnoses will be made available to database users in a manner that does not divulge any personally identifying information.

Figure 9:
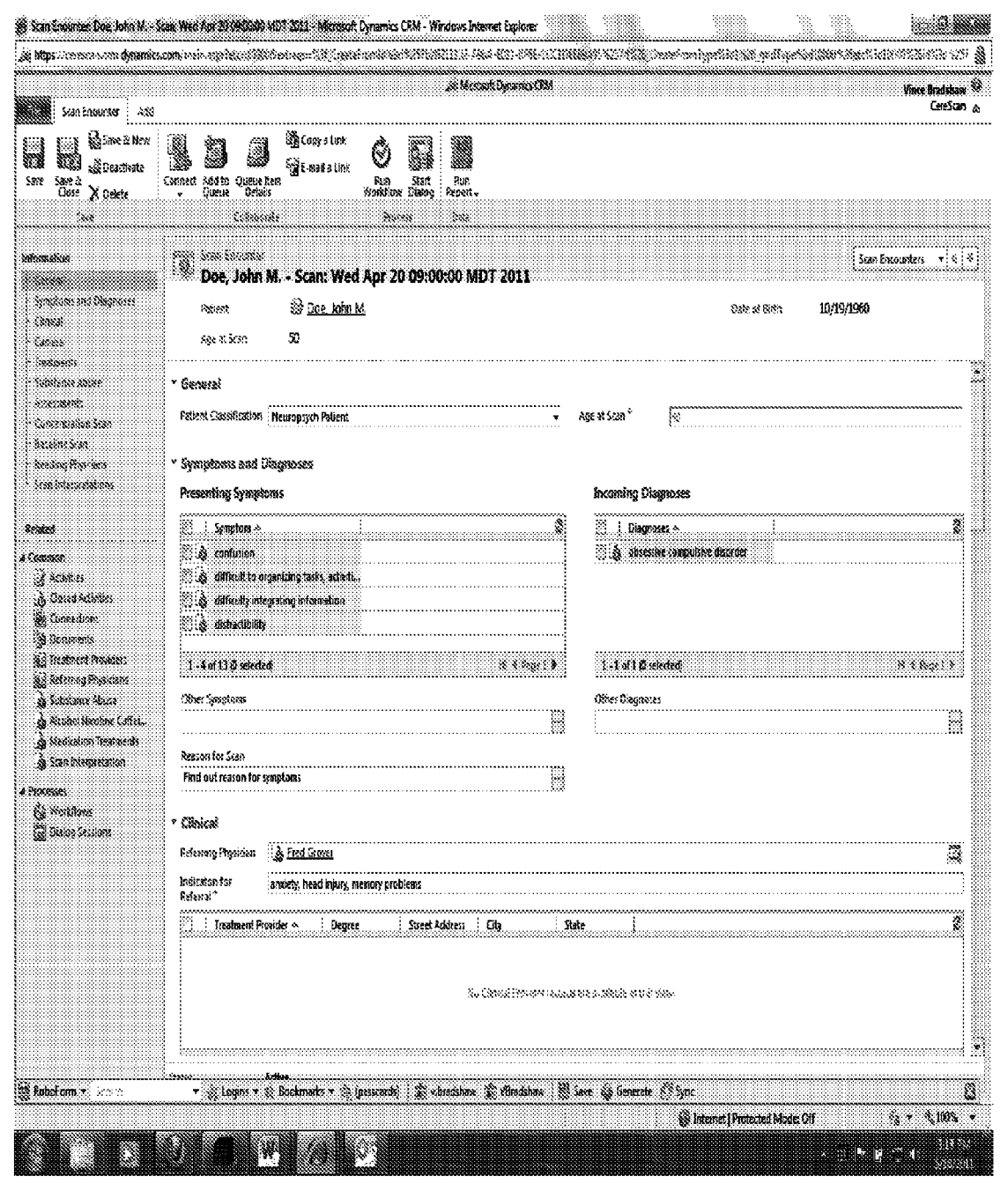

FIG. 9 is a scan encounter page according to an embodiment of the present invention. Like the page depicted in FIG. 8, the page of FIG. 9 may be part of an overall user interface to the database of brain scan information contemplated according to various embodiments of the present invention. Brain scan technologists or other database users may enter information relating to brain scan events in an interface page, such as that depicted in FIG. 9. Such data may be gathered and stored in the overall database. Information entered in the interface depicted in FIG. 9 may include, by way of non-limiting example, patient name, scan event date and time, identification of the scanning machine, a patient classification, a patient age at the scan event, presenting symptoms, other symptoms, an incoming diagnosis, other diagnoses, a reason for the associated scan, a referring physician, an indication for the referral, and demographic information of the referring physician(s). The presenting symptoms may be selected from a list of available symptoms, such as that available from a pre-populated drop-down menu. Multiple scan encounters may be entered in the page depicted in FIG. 9.

FIGS. 10-14 are flow charts according to various exemplary embodiments of the present invention. The methods depicted in FIGS. 10-14 may be implemented using, for example, what is commonly referred to in the art as Clinical Decision Support Systems (CDSS).

Figure 10:
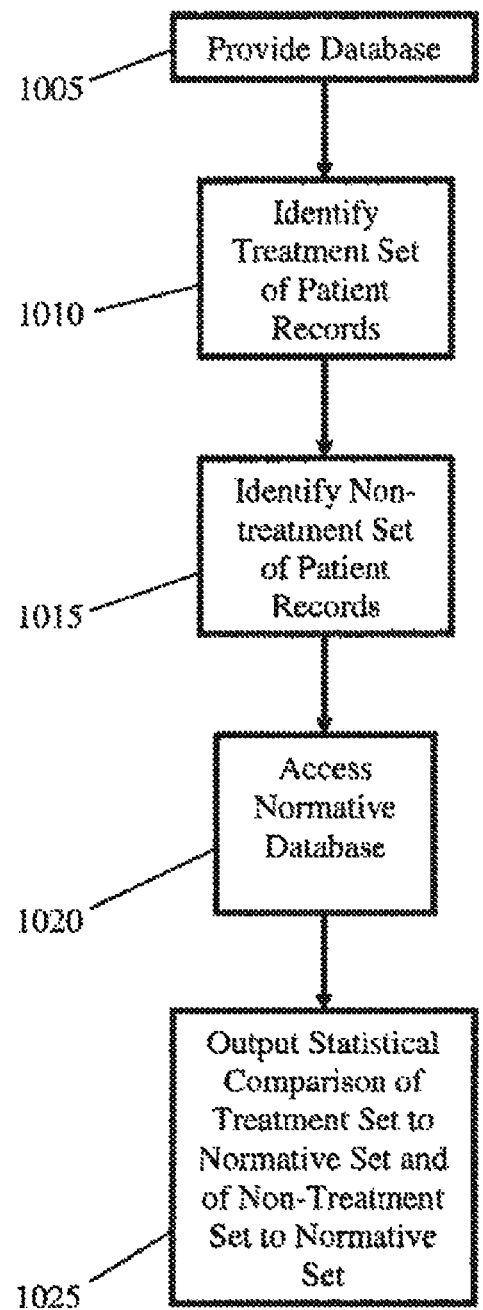
FIG. 10 is a flow chart according to an embodiment of the present invention.

FIG. 10 is a flow chart according to an embodiment of the present invention. Specifically, FIG. 10 illustrates a method of analyzing the pathophysiological basis of a chronic brain disease and/or the effectiveness of a certain treatment for the chronic brain disease. Once a chronic brain disease and putative treatment are identified, the process begins at block 1005, where a database may be provided. The database may include electronically stored brain scans of patients diagnosed with the chronic brain disease at issue. An exemplary such database is discussed in detail above with respect to FIG. 1.

At block 1010, the method identifies a treatment set of patient records in the provided database. The treatment set of patient records corresponds to patients that have been diagnosed with the chronic brain disease at issue and have received the putative treatment. In some embodiments, the step portrayed at block 1010 may be broken down into sub-steps as follows. A database user may generate an input to the database that is intended to identify the treatment set. Such an input may include a statement formatted in a language particular to databases, such as, by way of non-limiting example, in SQL. The statement may be compiled by the database into an executable query, which is then executed by the database. Such execution may reveal the patient records having the properties set forth in the database user's input, that is, the treatment set.

At block 1015, the method identifies a non-treatment set of patient records in the provided database. The non-treatment set of patient records corresponds to patient that have been diagnosed with the chronic brain disease but who have not received the putative treatment. In some embodiments, the step associated with block 1015 may be broken down into sub-steps. A database user may generate an input (e.g., a SQL statement) to the database that is intended to identify the non-treatment set. The input may be compiled by the database into an executable query, which is then executed by the database. Such execution may reveal the patient records having the properties set forth in the database user's input. In particular, the execution may identify a non-treatment set of patient records.

At block 1020, the method accesses a normative database. The normative database may be as discussed above in reference to FIG. 1. Thus, the normative database may include brain scans and/or other information associated with patients that have normal brain scans. Access may be over an electronic connection over one or more computer networks, such as the Internet. Alternately, or in addition, access may occur due to ownership of the normative database by the same entity that owns or controls the database provided at block 1005.

At block 1025, the method outputs statistical comparisons. Specifically, at block 1025, the method outputs a comparison of the treatment set of patient records to records in the normative database, and a comparison of the non-treatment set of patient records to the normative set of patient records. The statistical comparisons may include analyses of the average or mean variations in the perfusion levels in various regions of the brains of patients included in the treatment set versus the same or similar regions for patients in the non-treatment set, overall patterns or maps of the measured perfusion levels of patients in either set (treatment and non-treatment), as well as data, charts, and/or diagrams comparing the measured perfusion levels and their variations over time during the course of a given treatment program. Additionally, statistical comparisons may include analysis of current or prior symptoms, treatments, medications, and other non-image clinical information. Output may be in human readable form, e.g., on a computer monitor. Alternately, or in addition, output may be in machine-readable form, such as on a transitory or non-transitory computer readable medium.

Figure 11:
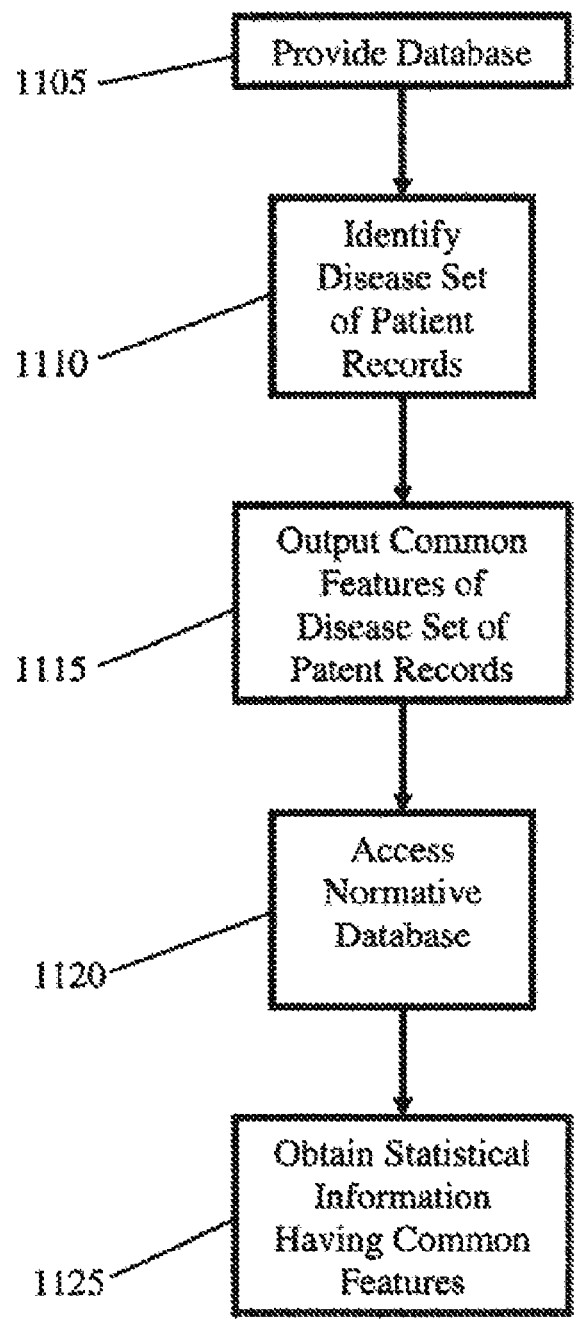
FIG. 11 is a flow chart according to an embodiment of the present invention.

FIG. 11 is a flow chart according to an embodiment of the present invention. Specifically, FIG. 11 illustrates a method of obtaining data for research of a chronic brain disease. Once a chronic brain disease is identified, the process begins at block 1105, where a database is provided. The database may include electronically stored brain scans of patients diagnosed with the chronic brain disease at issue. An exemplary such database is discussed in detail above with respect to FIG. 1.

At block 1110, the method identifies a disease set of patient records in the provided database. The disease set of patient records may correspond to patients that have been diagnosed with the chronic brain disease at issue. In some embodiments, the step portrayed at block 1110 may be broken down into sub-steps as follows. A database user may generate an input (e.g., a SQL statement) to the database that is intended to identify the disease set of patient records. The input may be compiled by the database into an executable query, which is then executed to reveal the patient records having the properties set forth in the database user's input. In particular, the execution may identify a disease set of patient records.

At block 1115, the method identifies and outputs common features of the disease set of patient records. In certain embodiments, the method may search patient medical information in the disease set of records for features that are common to a high percentage of the records. By way of non-limiting example, such features may include traumatic brain injury, exposure to toxic chemicals, oxygen deprivation, drug use, etc. A threshold percentage may be set by a user of the embodiments such that only features that are present in at least that percentage of records are identified. Exemplary percentages include, by way of non-limiting example, 20%, 30%, 40%, 50%, 60%, 70%, 80% and 90%. In some embodiments, at block 1115, the identified common features are output in human readable form in a manner that associates each feature with a corresponding percentage of disease records that include the feature in the associated patient medical information. Such information may be presented in chart form, as exemplified in a non-limiting fashion below.

TABLE 1

Features Identified in Disease Set of Records

| Feature | Percentage |
|---|---|
| Gender = Male | 93% |
| Past Trauma = Traumatic Brain Injury | 47% |
| Number with loss of consciousness | 42% |

At block 1120, the method accesses a normative database. The normative database may be as discussed above in reference to FIG. 1, including brain scans showing, for example, the normal perfusion patterns for the various regions of the brain for patients that have normal brain scans. Access may be over an electronic connection over one or more computer networks, such as the Internet. Alternately, or in addition, access may occur due to ownership of the normative database by the same entity that owns or controls the database provided at block 1105.

At block 1125, the method compares a brain scan of a patient in the disease set to corresponding normative brain scans to obtain statistical information. Such information may include, for example, measurements of the deviations (positive or negative) of one or a plurality of regions of a brain for a patient in the disease set as compared with the average or mean values for corresponding regions in the images in the normative database. In various exemplary embodiments, this information may be presented in a table as shown in FIG. 16. Using this data, the user may make an assessment of the level or degree of functionality in various parts or subparts of a patient's brain and then use that assessment to form a diagnosis of the causes or implications of evident injuries or abnormalities revealed in the patient's brain scans. Alternatively, the data may be presented in a summary form similar to that in Table 1.

Figure 12:
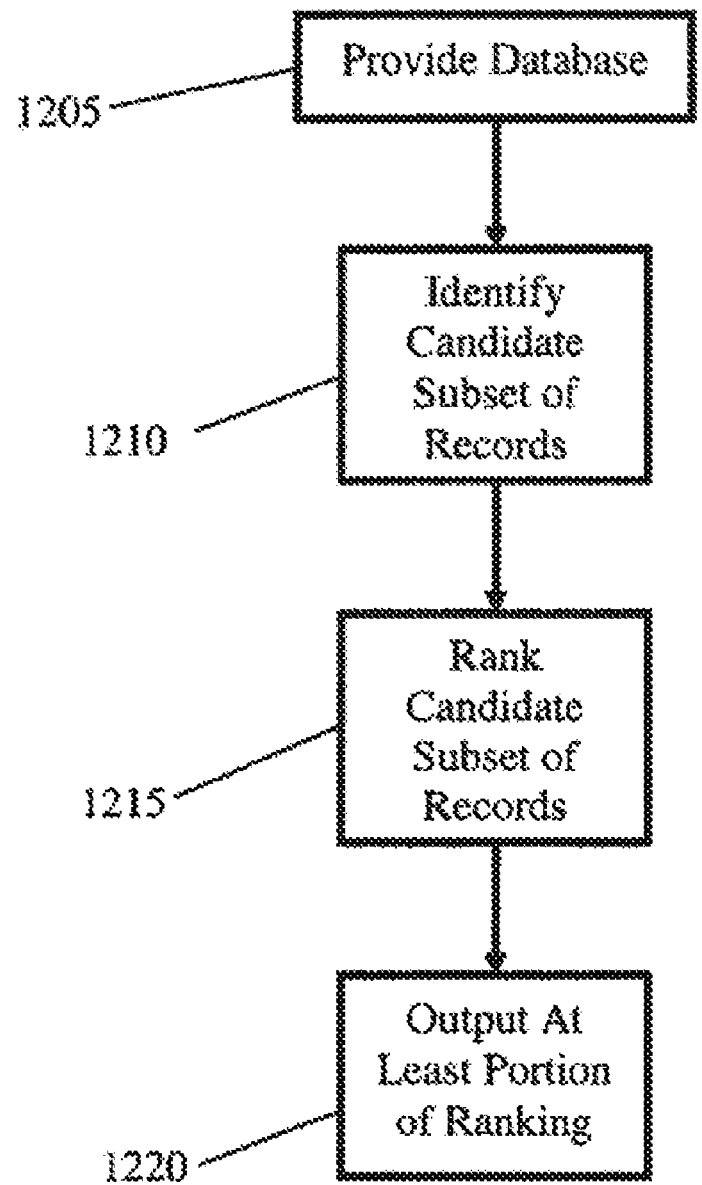
FIG. 12 is a flow chart according to an embodiment of the present invention.

FIG. 12 is a flow chart according to an embodiment of the present invention. Specifically, FIG. 12 illustrates a method of searching for symptoms identified in a clinical patient.

Once symptoms of a clinical patient are obtained by evaluation, referral, or other technique, the process begins at block 1205, where a database is provided. The database may include electronically stored brain scans of patients diagnosed with the chronic brain disease at issue. An exemplary such database is discussed in detail above with respect to FIG. 1.

At block 1210, the method identifies a candidate set of patient records in the provided database. The candidate set of patient records corresponds to patients that have similar symptoms to those of the clinical patient listed in the patient medical information of their associated records. In some embodiments, the step portrayed at block 1210 may be broken down into sub-steps as follows. A database user may generate an input (e.g., a SQL statement) to the database that is intended to specify the symptoms of the clinical patient. The input may be compiled by the database into an executable query, which is then executed to reveal the patient records having the properties set forth in the database user's input. In particular, the execution may identify a candidate set of patient records.

At block 1215, the method ranks the candidate set of records according to relevance to the clinical patient's symptoms. Such techniques are known to those of skill in the art and include, by way of non-limiting example, keyword weighting based on inverse frequency and statistical intent. Relevance ranking may be performed using, by way of non-limiting example, APACHE LUCENE CORE 3.3, available from lucene.apache.org. Thus, block 1215 may generally order the candidate set of patient records according to relevance.

At block 1220, the method outputs at least a portion of the ordered candidate set of patient records. The method may output the top few (e.g., 1, 3, 5, 10, 25, 50, 100) records. Output may be in human readable form, e.g., on a computer monitor. Alternately, or in addition, output may be in machine-readable form, such as on a transitory or non-transitory computer readable medium. The output may allow a doctor to evaluate whether the clinical patient suffers from one or more conditions whose presence is indicated in the ordered segment of the candidate patient records.

Some embodiments of the invention related to the embodiments of FIG. 12 allow a user to easily compare two or more brain scans. Such related embodiments may display two or more brain scan images sequentially in the same physical space. That is, such embodiments may display a first brain scan on a dynamic medium such as a computer monitor. The embodiments may then display a second scan in the same place as the first scan after removing the image of the first scan. Some embodiments allow a user to manually switch back and forth between images, e.g., by touching a key on a computer keyboard. Some embodiments allow a computer to automatically flip between images, e.g., at an adjustable rate (by way of non-limiting example, 0.25 hertz, 0.5 hertz, 1 hertz). Some embodiments allow for more than two such images. Advantages of the embodiments discussed in this paragraph include methods based on so-called "blink comparators" that can be used to easily detect differences between the displayed brain scans where differences will "blink" or "flicker" upon rapidly switching the images.

Figure 13:
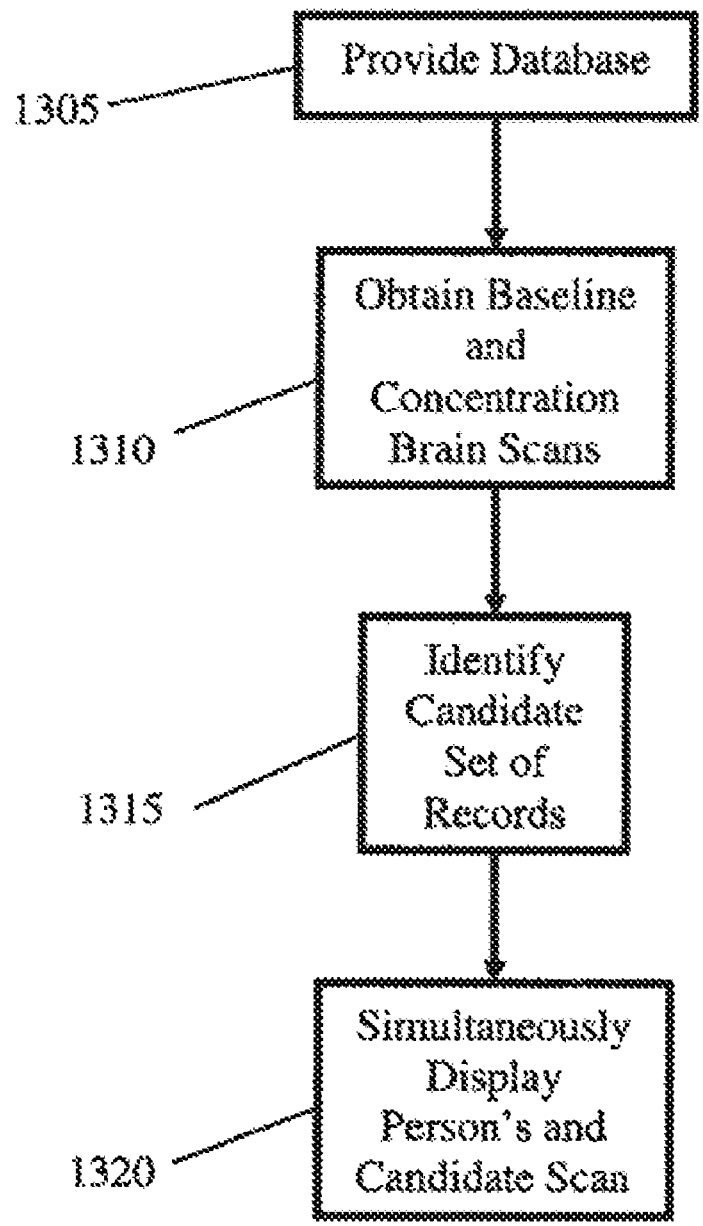
FIG. 13 is a flow chart according to an embodiment of the present invention.

FIG. 13 is a flow chart according to an embodiment of the present invention. Specifically, FIG. 13 illustrates a method of displaying brain scan information regarding a person. Once the person is identified, the process begins at block 1305, where a database is provided. The database may include electronically stored brain scans of patients diagnosed with the chronic brain disease at issue. An exemplary such database is discussed in detail above with respect to FIG. 1.

At block 1310, the method obtains at least two brain scans of the person. In particular, the method may obtain a baseline brain scan and a concentration brain scan. Both types of scans are discussed in detail above in reference to FIG. 1. In various exemplary embodiments, a technologist may obtain the scans using a SPECT scanner as discussed above.

At block 1315, the method identifies a candidate set of patient records in the provided database. The candidate set of patient records corresponds to patients that have similar symptoms to those of the person. In some embodiments, this step may be broken down into sub-steps. A database user may generate an input (e.g., a SQL statement) to the database that is intended to specify the symptoms of the person. The input may be compiled by the database into an executable query, which is then executed to reveal the patient records having the properties set forth in the database user's input. In particular, the execution may identify a candidate set of patient records.

At block 1320, the method displays both a brain scan of the person and a brain scan obtained at step 1315. Such display may be effectuated on, by way of non-limiting example, a computer monitor, a projection device, a printed poster, a plasma television set, a LCD television set, or a handheld device, such as a smart phone, tablet, personal digital assistant (PDA), or similar device. In some embodiments, the two brain scans are displayed side-by-side. In other embodiments, the two brain scans are displayed in a partially or completely overlapping manner, where at least one of the scans is at least partially transparent.

Embodiments of the invention discussed in reference to FIG. 13 may also be used, for example, to generate demonstrative exhibits in a legal proceeding. In such embodiments, the displaying step may include generating poster-sized hard copies in full color, or generating electronic images suitable for displaying in a large-scale forum, such as a court room.

Figure 14:
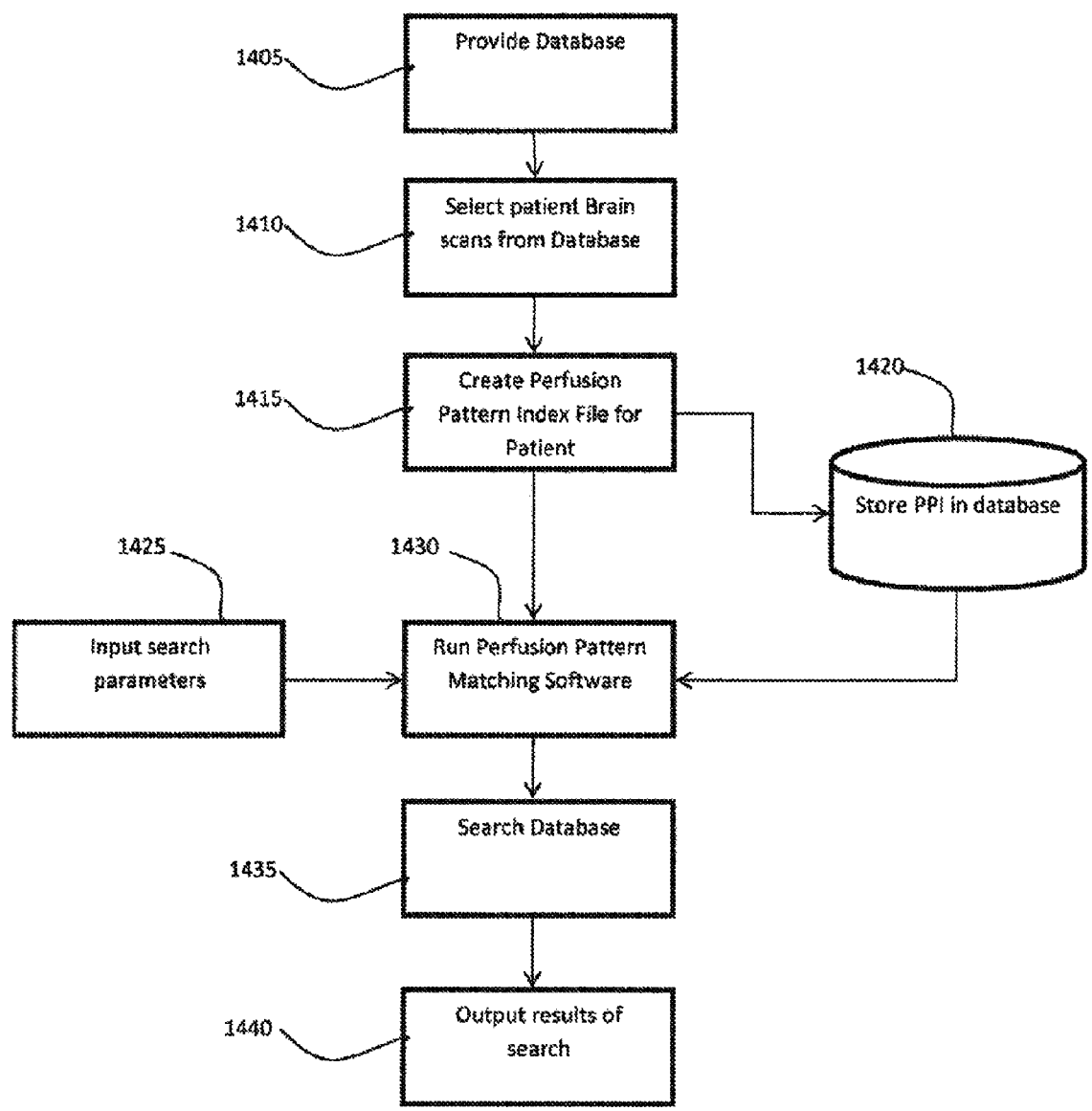
FIG. 14 is a flow chart according to an embodiment of the present invention.

FIG. 14 is a flow chart according to an embodiment of the present invention. Specifically, FIG. 14 illustrates a method of using pattern matching to analyze the pathophysiological basis of a chronic brain disease and/or the effectiveness of a proposed or previously administered treatment. The process begins at block 1405, where a database is provided. The database may include electronically stored brain scans of patients diagnosed with the chronic brain disease at issue. An exemplary such database is discussed in detail above with respect to FIG. 1.

At block 1410, the brain scans of a particular patient are selected from the provided database. In some embodiments, the step portrayed at block 1410 may be broken down into sub-steps as follows. A database user may generate an input to the database that is intended to identify the particular patient. Such an input may include a statement formatted in a language particular to databases, such as, by way of non-limiting example, SQL. The statement may be compiled by the database into an executable query, which is then executed by the database. Such execution may reveal the particular patient's records.

At block 1415, a brain Perfusion Pattern Index (PPI) computer file is created, which may contain the results of comparing one or more specific tomographic planes, slices, or segments (e.g., sagittal, coronal, transverse, curved plane) of the patient's brain with the corresponding tomographic planes, slices, or segments of the normative database, with the results being defined in the form of a two-dimensional table or a three-dimensional array. FIGS. 15A-D depict an exemplary embodiment of such a table. The cells in the table or array may contain statistically derived deviations between the patient's brain and the normal brain for one or more regions, with the values expressed as standard deviations, arithmetic means, or other mathematical expressions. The cells in the PPI table or array may represent variable areas or regions of interest within each plane and define individual voxels or groupings of voxels to encompass specific areas or volumes of the brain topology. The table or array cells may be identified using a coordinate-based mapping system (e.g., X-Y-Z or radial) or alternatively may be assigned easily remembered names or alphanumeric identifiers. In various exemplary embodiments, values (e.g., predetermined integers) representing the differences in brain perfusion levels may be used in the calculations. These differences may be mapped to particular regions of interest in the brain. For example, as shown in FIGS. 15A-D, one comparison may correspond to the "Anterior Cerebral-Left" portion of the brain, while another may correspond to the "Cerebral Cortex-Left" portion of the brain. Thus, if a user (e.g., a physician) is interested in a particular area of the brain, he or she can easily access the data for that area. Also, in various exemplary embodiments, a color display may be generated showing the patient's brain scans, the brain scans from the normative database, and/or the comparison data between the two as levels of color intensity.

An appropriately trained user (e.g., a physician) who has expertise with brain anatomy and functional neuroscience, for example, may use the data in FIGS. 15A-D to perform a logical analysis of abnormal functions in the brain in order to formulate a diagnosis and/or recommend treatment. Similarly, one or more computer programs may use data similar to that portrayed in FIGS. 15A-D to develop mathematical constructions of a patient's brain scan for comparison with similar constructions of other patients' brain scans. Referring to FIGS. 15A-D, an example of a computer instruction might be: "Find all the patients in a disease set in database 100 where the values for 'Anterior Cerebral-Left' are less than N1 and where the values for 'Cerebral Cortex-Left' are less than N2, then display a list of the patient's medical identification numbers on a computer monitor or display." One or more computer programs may be provided in the form of a Clinical Decision Support System to assist in diagnosing patients with chronic brain diseases by grouping instruction sets to search the database for patients with similar perfusion patterns and perform various data analyses of their demographics, previous and current symptoms, diagnoses, treatments, and clinical outcomes to provide insights to aid in clinical diagnoses and treatment evaluations. Such instruction sets may be pre-programmed or made available on an ad hoc basis using various input methods (e.g., point and click, drop down menu, or text entry).

Returning to FIG. 14, at block 1420, the PPI for the patient is stored with the patient's medical record in the database to serve as a mathematical index for subsequent search and comparison operations.

The process illustrated in blocks 1405-1420 may be repeated for one or more other patients, resulting in a database comprising, among other things, multiple PPI files.

It will be recognized by a person of ordinary skill in the art that various commercially available computer software packages and algorithms may be used for pattern matching in images, such as the Medical Image Processing, Analysis, and Visualization (MIPAV) application, offered by the National Institutes of Health. Also, significant research has been published regarding the use of Support Vector Machines for Regression (SVR) for performing brain image analysis and pattern recognition. Such software and algorithms may be used for pattern matching as described herein. It will also be recognized, however, that image matching may be computationally intensive and slow. The substitution of a mathematical table or array indexing scheme, as described herein, may increase search speed and reduce the processing power required to perform pattern matching.

At block 1425, a query is made to a Perfusion Pattern Matching Software (PPMS) rules engine by inputting a specific patient's PPI and specifying user-variable search parameters, such as defined coordinates, region(s) of interest, or limits of variability. At block 1430, the PPMS executes, and at block 1435, the PPMS rules engine searches all or a subset of other patients within the database for those patients whose PPIs match the subject patient within the user-selected range. At block 1440, the PPMS outputs for subsequent analysis a list of the patients whose PPIs fall within the search parameters in either human or machine readable format.

Once patients with similar symptoms, histories, or other criteria are selected from the database, either through the process illustrated in blocks 1425-1440 or by a user inputting a request for a set of patients, the PPMS rules engine at block 1445 uses the set of patient database identifiers (e.g., medical record numbers), along with user-variable search parameters and variability limits, to calculate an average or mean PPI (aPPI) for the aggregate group of patients, using standard statistical methods. At block 1450, the PPMS rules engine scores each patient based on their consistency with the aPPI and the user-selected parameters, and returns the result in human or machine readable format. The aPPI may be retained as a library file in the PPMS for future use in searching the database and/or comparing and scoring additional patients.

FIG. 16 is a portion of an example patient analysis report according to an embodiment of the present invention. Using the methods and systems described herein, reports may be compiled and presented to the user in, for example, a graphical display. The report depicted in FIG. 16, for example, shows an analysis of 374 patients who had brain scans in light of several variables. The report shows the reason for the brain scan, the percentage of the scanned group, the number of patients with a history of hypoxia, information regarding the diagnosis of the incoming physician, and information regarding the findings of the outgoing physician. The report may include an area where a user, such as Dr. Smith, may input preliminary observations based on the compiled data. It is to be appreciated that any of the data discussed herein may be compiled and/or displayed in a report of any type, including that depicted in FIG. 16.

Though this application generally refers to SPECT scans, any other neuroimaging study may be implemented in addition or in the alternative, such as Positron Emission Tomography (PET), Functional Magnetic Resonance Imaging (fMRI), or Diffusion Magnetic Resonance Imaging (e.g., diffusion weighted imaging or diffusion tensor imaging). Any type of brain scan, and any combination of brain scans (e.g., SPECT scan and fMRI scan), may be used.

According to various embodiments, data storage may take any of many different forms. Data may be stored via network accessible storage and may be local, remote, or a combination thereof. Data storage may utilize a redundant array of inexpensive disks (RAID), tape, disk, a storage area network (SAN), an interne small computer systems interface (iSCSI) SAN, a Fibre Channel SAN, a common Internet File System (CIFS), network attached storage (NAS), a network file system (NFS), or other computer accessible storage.

According to various embodiments, the database may be implemented using, by way of non-limiting example, an Oracle database, a Microsoft SQL Server database, a DB2 database, a MySQL database, a Sybase database, an object oriented database, a hierarchical database, or other database.

It is to be appreciated that the set of instructions, e.g., the software, that configures the computer operating system to perform the operations described above may be contained on any of a wide variety of media or medium, as desired. Further, any data that is processed by the set of instructions might also be contained on any of a wide variety of media or medium. That is, the particular medium, that is, the memory in the processing machine, utilized to hold the set of instructions or the data used in the invention may take on any of a variety of physical forms or transmissions, for example. Illustratively, the medium may be in the form of paper, paper transparencies, a compact disk, a DVD, an integrated circuit, a hard disk, a floppy disk, an optical disk, a magnetic tape, a RAM, a ROM, a PROM, a EPROM, a wire, a cable, a fiber, communications channel, a satellite transmissions or other remote transmission, as well as any other medium or source of data that may be read by a computer.

It is also to be appreciated that the various components described herein, such as a computer running executable computer software and a database, may be located remotely and may communicate with each other via electronic transmission over one or more computer networks. As referred to herein, a network may include, but is not limited to, a wide area network (WAN), a local area network (LAN), a global network such as the Internet, a telephone network such as a public switch telephone network, a wireless communication network, a cellular network, an intranet, or the like, or any combination thereof. In various exemplary embodiments, a network may include one, or any number of the exemplary types of networks mentioned above, operating as a stand alone network or in cooperation with each other. Use of the term network herein is not intended to limit the network to a single network.

In the preceding specification, various preferred embodiments have been described with references to the accompanying drawings. It will, however, be evident that various modifications and changes may be made thereto, and additional embodiments may be implemented, without departing from the broader scope of invention as set forth in the claims that follow. The specification and drawings are accordingly to be regarded in an illustrative rather than restrictive sense.

We claim:

1. A system comprising:
an electronic database comprising a plurality of records, each of the plurality of records associated with a respective patient, each of the plurality of records comprising: one or more digital representations of a baseline functional brain scan image comprising a plurality of image planes for a respective patient, a digital representation of a medical history of a respective patient, a digital representation of demographic information of a respective patient, and a digital representation of a set of clinical symptoms of a respective patient; and
one or more computer processors that:
receive a first input from a database user, convert the first input into a first query, and execute the first query, wherein a first subset of the plurality of records is identified, the first subset of the plurality of records corresponding to a treatment set of patients, each of whose respective database records indicate a diagnosis of a brain condition and that the respective patient in the treatment set received a treatment,
receive a second input from a database user, convert the second input into a second query, and execute the second query, wherein a second subset of the plurality of database records is identified, the second subset of the plurality of database records corresponding to a set of patients that did not receive the treatment, each of whose respective database records indicate a diagnosis of the brain condition,
output a first statistical comparison of the first subset of the plurality of database records to a normative set of electronic records corresponding to patients that were not diagnosed with the brain condition and did not receive the treatment; and
output, for each of the one or more features, a percentage of the records in the normative database of electronic records in which the one or more features are present, wherein the percentage of the records further comprises a percentage of disease database records in which the one or more features are present and a percentage of normative database records in which the one or more features are present.

2. The system of claim 1, wherein the one or more computer processors further:
output a second statistical comparison of the second subset of the plurality of database records to the normative set of electronic records, wherein information regarding one or more of the basis of the brain condition and effectiveness of the treatment for the brain condition are analyzed based at least in part on the first statistical comparison and the second statistical comparison.

3. The system of claim 1, wherein each digital representation of a baseline functional brain scan image comprises a set of location-specific values reflecting differences from normal.

4. The system of claim 1, wherein the one or more computer processors further identify and output one or more features present in at least a percentage of a condition subset of the plurality of records.

5. The system of claim 1, further comprising a nuclear imaging camera configured to obtain a baseline brain scan of the person comprising a plurality of image planes and a concentration brain scan image of the person comprising a plurality of image planes.

6. The system of claim 1, wherein the one or more computer processors further:
receive an input reflecting a set of symptoms of the person, convert the input into a first query, and execute the first query, wherein a candidate subset of the patient database records is identified, the candidate subset of the patient database records corresponding to a set of patients whose respective patient database records include the set of symptoms of the person, and
cause the display of:
at least one baseline brain scan image and at least one concentration scan image, and
at least one brain scan image of the candidate subset of the patient database records.

7. The system of claim 1, wherein one or more computer processors further:
receive an input from a database user, wherein the input comprises an identifier for a first patient having an index file in the plurality of records, and one or more search parameters, wherein the index file comprises brain measurements compared to norm values, convert the input into a query, and execute the query, wherein a subset of the plurality of records is identified, the subset of the plurality of records corresponding to a set of patients, each of whose respective database records indicate an index file that substantially matches the first patient's index file based on the one or more search parameters, determine an average index file for the subset of the plurality of records, and output a comparison of the index file of each patient in the set of patients to the average index file.

8. The system of claim 7, wherein the index file comprises brain measurements compared to norm values.

9. The system of claim 1, wherein the one or more computer processors further:

create an index file for a first patient having at least one record in the plurality of records, wherein the index file comprises brain measurements compared to norm values and wherein the index file is created at least in part by determining digital levels of statistical deviation in brain measurement levels between the brain scans of the first patient and normative brain scans of patients with no indications of chronic or acute brain conditions, store the index file in the plurality of records, execute a query, where a subset of the plurality of records is identified, the subset of the plurality of records corresponding to a set of patients, each of whose respective database records indicate an index file that substantially matches the first patient's index file based on one or more search parameters, determine an average index file for the subset of the plurality of records, and output a comparison of the index file of each patient in the set of patients to the average index file.

10. The system of claim 9, wherein the index file is a multi-dimensioned table or array.

11. The system of claim 10, wherein the index file is created using values representing differences in brain measurement levels between the brain scans of the first patient and the normative brain scans.

12. The system of claim 9, wherein each digital representation of a baseline functional brain scan image comprises a set of location-specific values reflecting differences from normal.

13. The system of claim 1, wherein one or more computer processors further:

receive an input from a database user, wherein the input comprises an identifier for a first patient having an index file in the plurality of records, and one or more search parameters wherein the index file comprises brain measurements compared to norm values.

14. The system of claim 1, wherein one or more computer processors further:

create an index file for a first patient having at least one record in the plurality of records, wherein the index file comprises brain measurements compared to norm values and wherein the index file is created by determining digital levels of statistical deviation in brain perfusion levels between the brain scans of the first patient and normative brain scans of patients with no indications of chronic brain conditions.

15. The system of claim 1, wherein each digital representation of a baseline functional brain scan image comprises a set of location-specific values reflecting differences from normal.

16. A system comprising:

an electronic database comprising a plurality of records, each of the plurality of records associated with a respective patient, each of the plurality of records comprising: one or more digital representations of a baseline functional brain scan image comprising a plurality of image planes for a respective patient, a digital representation of a medical history of a respective patient, a digital representation of demographic information of a respective patient, and a digital representation of a set of clinical symptoms of a respective patient; and one or more computer processors that:

receive a first input from a database user, convert the first input into a first query, and execute the first query, wherein a first subset of the plurality of records is identified, the first subset of the plurality of records corresponding to a treatment set of patients, each of whose respective database records indicate a diagnosis of a brain condition and that the respective patient in the treatment set received a treatment, receive a second input from a database user, convert the second input into a second query, and execute the second query, wherein a second subset of the plurality of database records is identified, the second subset of the plurality of database records corresponding to a set of patients that did not receive the treatment, each of whose respective database records indicate a diagnosis of the brain condition, output a first statistical comparison of the first subset of the plurality of database records to a normative set of electronic records corresponding to patients that were not diagnosed with the brain condition and did not receive the treatment rank a candidate subset of the patient database records according to relevancy to the set of symptoms of the patient, wherein a ranking is produced, and output in user viewable form at least a portion of the ranking, wherein a possible diagnosis of the clinical patient is provided.

17. The system of claim 16, wherein the one or more computer processors further:

output a second statistical comparison of the second subset of the plurality of database records to the normative set of electronic records, wherein information regarding one or more of the basis of the brain condition and effectiveness of the treatment for the brain condition are analyzed based at least in part on the first statistical comparison and the second statistical comparison.

18. The system of claim 16, wherein each digital representation of a baseline functional brain scan image comprises a set of location-specific values reflecting differences from normal.

19. The system of claim 16, wherein the one or more computer processors further identify and output one or more features present in at least a percentage of a condition subset of the plurality of records.

20. The system of claim 16, further comprising a nuclear imaging camera configured to obtain a baseline brain scan of the person comprising a plurality of image planes and a concentration brain scan image of the person comprising a plurality of image planes.

21. The system of claim 16, wherein the one or more computer processors further:
receive an input reflecting a set of symptoms of the person, convert the input into a first query, and execute the first query, wherein a candidate subset of the patient database records is identified, the candidate subset of the patient database records corresponding to a set of patients whose respective patient database records include the set of symptoms of the person, and
cause the display of:
at least one baseline brain scan image and at least one concentration scan image, and
at least one brain scan image of the candidate subset of the patient database records.

22. The system of claim 16, wherein one or more computer processors further:
receive an input from a database user, wherein the input comprises an identifier for a first patient having an index file in the plurality of records, and one or more search parameters, wherein the index file comprises brain measurements compared to norm values,
convert the input into a query, and execute the query, wherein a subset of the plurality of records is identified, the subset of the plurality of records corresponding to a set of patients, each of whose respective database records indicate an index file that substantially matches the first patient's index file based on the one or more search parameters,
determine an average index file for the subset of the plurality of records, and
output a comparison of the index file of each patient in the set of patients to the average index file.

23. The system of claim 22, wherein the index file comprises brain measurements compared to norm values.

24. The system of claim 16, wherein the one or more computer processors further:
create an index file for a first patient having at least one record in the plurality of records, wherein the index file comprises brain measurements compared to norm values and wherein the index file is created at least in part by determining digital levels of statistical deviation in brain measurement levels between the brain scans of the first patient and normative brain scans of patients with no indications of chronic or acute brain conditions,
store the index file in the plurality of records,
execute a query, where a subset of the plurality of records is identified, the subset of the plurality of records corresponding to a set of patients, each of whose respective database records indicate an index file that substantially matches the first patient's index file based on one or more search parameters,
determine an average index file for the subset of the plurality of records, and
output a comparison of the index file of each patient in the set of patients to the average index file.

25. The system of claim 24, wherein the index file is a multi-dimensional table or array.

26. The system of claim 25, wherein the index file is created using values representing differences in brain measurement levels between the brain scans of the first patient and the normative brain scans.

27. The system of claim 24, wherein each digital representation of a baseline functional brain scan image comprises a set of location-specific values reflecting differences from normal.

28. The system of claim 16, wherein one or more computer processors further:
receive an input from a database user, wherein the input comprises an identifier for a first patient having an index file in the plurality of records, and one or more search parameters wherein the index file comprises brain measurements compared to norm values.

29. The system of claim 16, wherein one or more computer processors further:
create an index file for a first patient having at least one record in the plurality of records, wherein the index file comprises brain measurements compared to norm values and wherein the index file is created by determining digital levels of statistical deviation in brain measurement levels between the brain scans of the first patient and normative brain scans of patients with no indications of chronic or acute brain conditions.

30. The system of claim 16, wherein each digital representation of a baseline functional brain scan image comprises a set of location-specific values reflecting differences from normal.

31. A method comprising:
providing an electronic database comprising a plurality of records, each of the plurality of records associated with a respective patient, each of the plurality of records comprising: one or more digital representations of a baseline functional brain scan image comprising a plurality of image planes for a respective patient, a digital representation of a medical history of a respective patient, a digital representation of demographic information of a respective patient, and a digital representation of a set of clinical symptoms of a respective patient;
receiving a first input from a database user;
converting the first input into a first query;
executing the first query, wherein a first subset of the plurality of records is identified, the first subset of the plurality of records corresponding to a treatment set of patients, each of whose respective database records indicate a diagnosis of the brain condition and that the respective patient in the treatment set received a treatment;
receiving a second input from a database user;
converting the second input into a second query;
executing the second query, wherein a second subset of the plurality of database records is identified, the second subset of the plurality of database records corresponding to a set of patients that did not receive the treatment, each of whose respective database records indicate a diagnosis of the brain condition;
outputting a first statistical comparison of the first subset of the plurality of database records to a normative set of electronic records corresponding to patients that were not diagnosed with the brain condition and did not receive the treatment
wherein the database user is presented with one or more features, a percentage of disease database records in which the one or more features are present, and a percentage of normative database records in which the one or more features are present.

32. The method of claim 31, wherein each digital representation of a baseline functional brain scan image comprises a set of location-specific values reflecting differences from normal.

33. A method comprising:
providing an electronic database comprising a plurality of records, each of the plurality of records associated with a respective patient, each of the plurality of records comprising: one or more digital representations of a baseline functional brain scan image comprising a plurality of image planes for a respective patient, a digital representation of a medical history of a respective patient, a digital representation of demographic information of a respective patient, and a digital representation of a set of clinical symptoms of a respective patient;
receiving a first input from a database user;
converting the first input into a first query;
executing the first query, wherein a first subset of the plurality of records is identified, the first subset of the plurality of records corresponding to a treatment set of patients, each of whose respective database records indicate a diagnosis of the brain condition and that the respective patient in the treatment set received a treatment;
receiving a second input from a database user;
converting the second input into a second query;
executing the second query, wherein a second subset of the plurality of database records is identified, the second subset of the plurality of database records corresponding to a set of patients that did not receive the treatment, each of whose respective database records indicate a diagnosis of the brain condition;
outputting a first statistical comparison of the first subset of the plurality of database records to a nonnative set of electronic records corresponding to patients that were not diagnosed with the brain condition and did not receive the treatment;
ranking a candidate subset of the plurality of records according to relevancy to a set of symptoms of the respective patient, wherein a ranking is produced; and
outputting in a user viewable form at least a portion of the ranking and a possible diagnosis of the respective patient.

34. The method of claim 33, wherein each digital representation of a baseline functional brain scan image comprises a set of location-specific values reflecting differences from normal.

* * * * *